US010639068B2

(12) United States Patent
Parihar et al.

(10) Patent No.: US 10,639,068 B2
(45) Date of Patent: *May 5, 2020

(54) TROCAR WITH OBLIQUE NEEDLE INSERTION PORT AND PERPENDICULAR SEAL LATCH

(71) Applicant: ETHICON LLC, Guaynabo, PR (US)

(72) Inventors: Shailendra K. Parihar, Mason, OH (US); Jason L. Harris, Lebanon, OH (US); Frederick E. Shelton, IV, Hillsboro, OH (US)

(73) Assignee: Ethicon LLC, Guaynabo, PR (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/637,683

(22) Filed: Jun. 29, 2017

(65) Prior Publication Data

US 2019/0000505 A1    Jan. 3, 2019

(51) Int. Cl.
*A61B 17/34*    (2006.01)
*A61B 17/04*    (2006.01)
(Continued)

(52) U.S. Cl.
CPC ...... *A61B 17/3423* (2013.01); *A61B 17/0057* (2013.01); *A61B 17/3421* (2013.01);
(Continued)

(58) Field of Classification Search
CPC ............ A61B 17/3423; A61B 17/3462; A61B 17/0483; A61B 17/3498; A61B 2017/3445; A61B 17/3474; A61B 2017/00637
See application file for complete search history.

(56) References Cited

U.S. PATENT DOCUMENTS 3,877,434 A    4/1975  Ferguson et al.
3,995,619 A    12/1976 Glatzer
(Continued)

FOREIGN PATENT DOCUMENTS

EP    2 168 511 A2    3/2010
EP    3 225 202 A1    10/2017
(Continued)

OTHER PUBLICATIONS

U.S. Appl. No. 15/637,688, filed Jun. 29, 2017.
(Continued)

*Primary Examiner* — Theodore J Stigell
(74) *Attorney, Agent, or Firm* — Frost Brown Todd LLC

(57) ABSTRACT

A surgical access device includes a cannula having proximal and distal ends and a cannula lumen. A housing assembly coupled to the proximal end includes a proximal housing and a latch ring having a user engagement feature. The latch ring is rotatable by the user engagement feature to selectively couple and decouple the proximal housing with the cannula. An interior of the housing assembly communicates with the cannula lumen to define a working channel extending along a central axis of the surgical access device. First and second needle ports open to the working channel through respective first and second side portions of the surgical access device. Each needle port is configured to direct a suture needle across the working channel at an oblique angle relative to the central device axis. The user engagement feature is circumferentially offset from each of the first and second needle ports.

20 Claims, 18 Drawing Sheets

(51) Int. Cl.
*A61B 17/00* (2006.01)
*A61B 17/06* (2006.01)

(52) U.S. Cl.
CPC ....... *A61B 17/0469* (2013.01); *A61B 17/0482* (2013.01); *A61B 17/0483* (2013.01); *A61B 17/3462* (2013.01); *A61B 17/3474* (2013.01); *A61B 17/3498* (2013.01); *A61B 2017/00637* (2013.01); *A61B 2017/00663* (2013.01); *A61B 2017/06042* (2013.01); *A61B 2017/3445* (2013.01)

(56) References Cited

U.S. PATENT DOCUMENTS

| | | | |
|---|---|---|---|
| 5,792,135 | A | 8/1998 | Madhani et al. |
| 5,817,084 | A | 10/1998 | Jensen |
| 5,878,193 | A | 3/1999 | Wang et al. |
| 6,231,565 | B1 | 5/2001 | Tovey et al. |
| 6,364,888 | B1 | 4/2002 | Niemeyer et al. |
| 6,783,524 | B2 | 8/2004 | Anderson et al. |
| 7,524,320 | B2 | 4/2009 | Tierney |
| 7,691,098 | B2 | 4/2010 | Wallace et al. |
| 7,803,135 | B2 | 9/2010 | Franer |
| 7,806,891 | B2 | 10/2010 | Nowlin et al. |
| 7,981,092 | B2 | 7/2011 | Duke |
| 8,226,553 | B2 | 7/2012 | Shelton, IV et al. |
| 8,251,900 | B2 | 8/2012 | Ortiz et al. |
| 8,479,969 | B2 | 7/2013 | Shelton, IV |
| 8,568,362 | B2 | 10/2013 | Moreno, Jr. et al. |
| 8,573,461 | B2 | 11/2013 | Shelton, IV et al. |
| 8,573,465 | B2 | 11/2013 | Shelton, IV |
| 8,579,807 | B2 | 11/2013 | Moreno et al. |
| 8,602,288 | B2 | 12/2013 | Shelton, IV et al. |
| 8,616,431 | B2 | 12/2013 | Timm et al. |
| 8,636,686 | B2 | 1/2014 | Minnelli et al. |
| 8,668,711 | B2 | 3/2014 | Teichtmann et al. |
| 8,690,831 | B2 | 4/2014 | Duke |
| 8,783,541 | B2 | 7/2014 | Shelton, IV et al. |
| 8,800,838 | B2 | 8/2014 | Shelton, IV |
| 8,820,605 | B2 | 9/2014 | Shelton, IV |
| 8,844,789 | B2 | 9/2014 | Shelton, IV et al. |
| 9,301,759 | B2 | 4/2016 | Spivey et al. |
| 9,687,226 | B2 | 6/2017 | Hodgkinson et al. |
| 9,700,303 | B2 | 7/2017 | Prior et al. |
| 2005/0021055 | A1 | 1/2005 | Toubia et al. |
| 2006/0276751 | A1* | 12/2006 | Haberland ......... A61B 17/3462 604/167.01 |
| 2007/0004968 | A1 | 1/2007 | Bonadio et al. |
| 2008/0200950 | A1 | 8/2008 | Wohlert |
| 2011/0237901 | A1* | 9/2011 | Duke ................. A61B 17/3462 600/208 |
| 2015/0038793 | A1* | 2/2015 | Prior .................... A61M 5/329 600/204 |
| 2017/0281154 | A1 | 10/2017 | Hess et al. |
| 2019/0000504 | A1 | 1/2019 | Terefe et al. |

FOREIGN PATENT DOCUMENTS

| | | |
|---|---|---|
| WO | WO 2010/000033 A1 | 1/2010 |
| WO | WO 2012/034131 A2 | 3/2012 |
| WO | WO 2013/105993 A2 | 7/2013 |
| WO | WO 2014/169215 A2 | 10/2014 |

OTHER PUBLICATIONS

U.S. Appl. No. 15/637,690, filed Jun. 29 2017.
U.S. Appl. No. 15/637,696, filed Jun. 29, 2017.
U.S. Appl. No. 15/637,702, filed Jun. 29 2017.
U.S. Appl. No. 15/637,707, filed Jun. 29, 2017.
U.S. Appl. No. 15/637,712, filed Jun. 29 2017.
U.S. Appl. No. 15/637,735, filed Jun. 29, 2017.
U.S. Appl. No. 15/637,778, filed Jun. 29 2017.
Partial European Search Report and Provisional Written Opinion dated Oct. 5, 2018 for Application No. EP 18180458.4, 16 pgs.
European Search Report, Extended, and Written Opinion dated Jan. 29, 2019 for Application No. EP 18180458.4, 14 pgs.
International Search Report and Written Opinion dated Feb. 14, 2019 for Application No. PCT/IB2018/054522, 24 pgs.

* cited by examiner

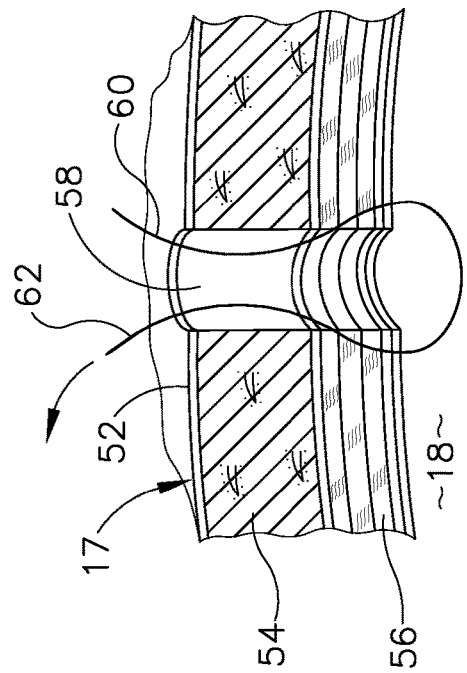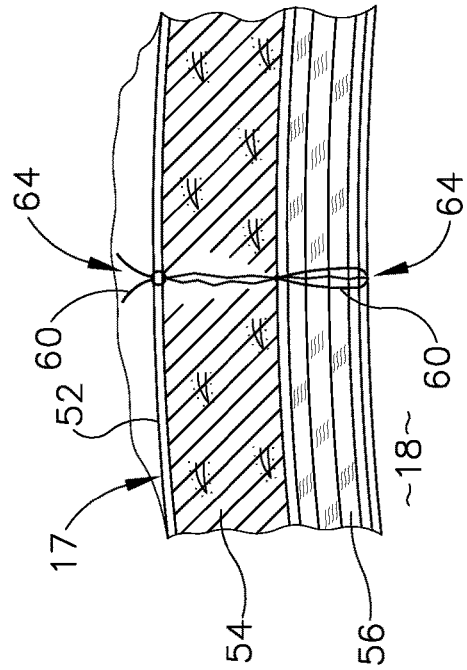
Fig.4A  Fig.4B
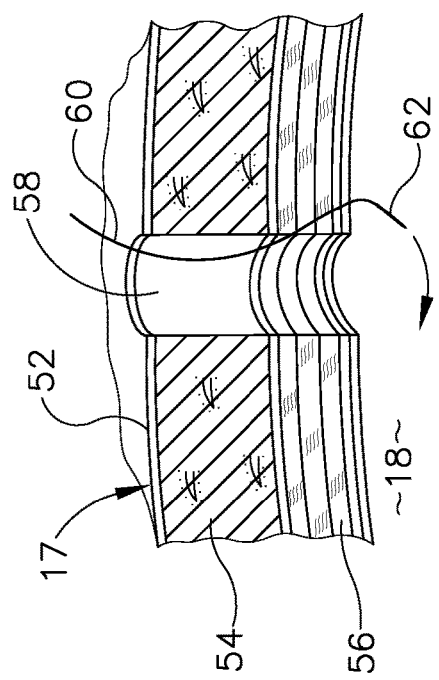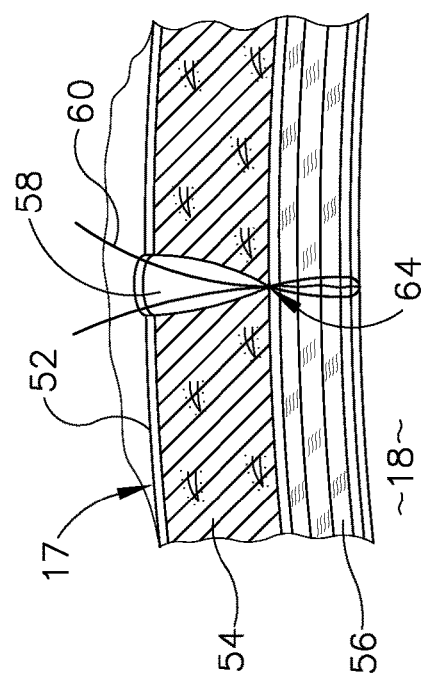
Fig.4C  Fig.4D

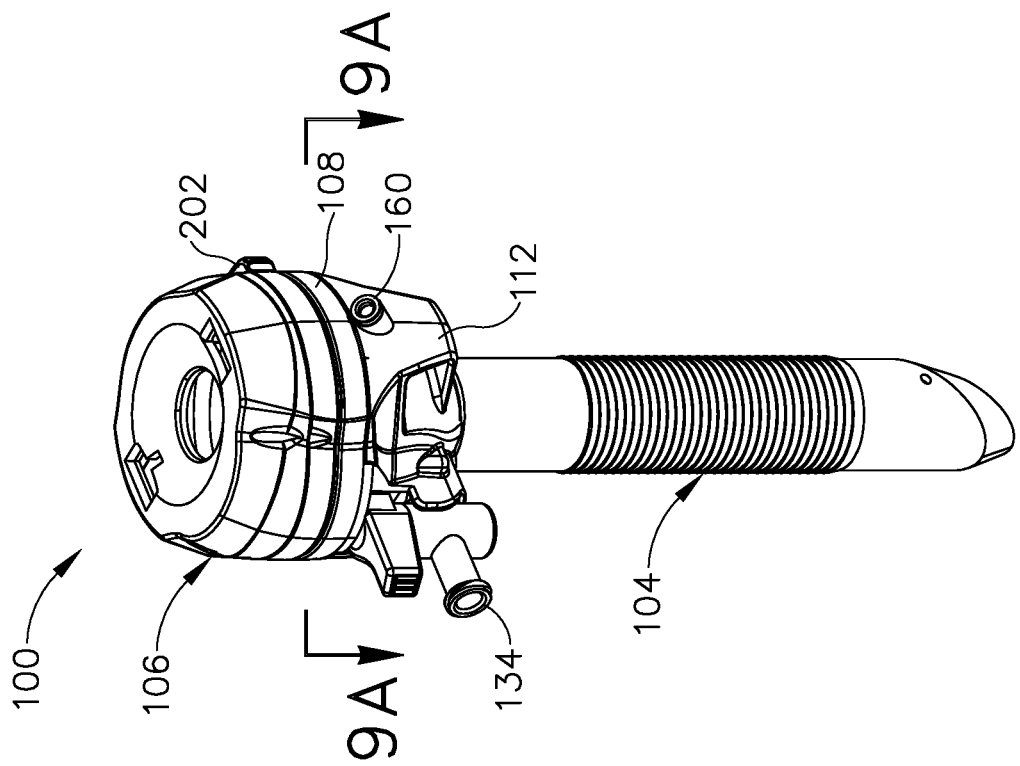
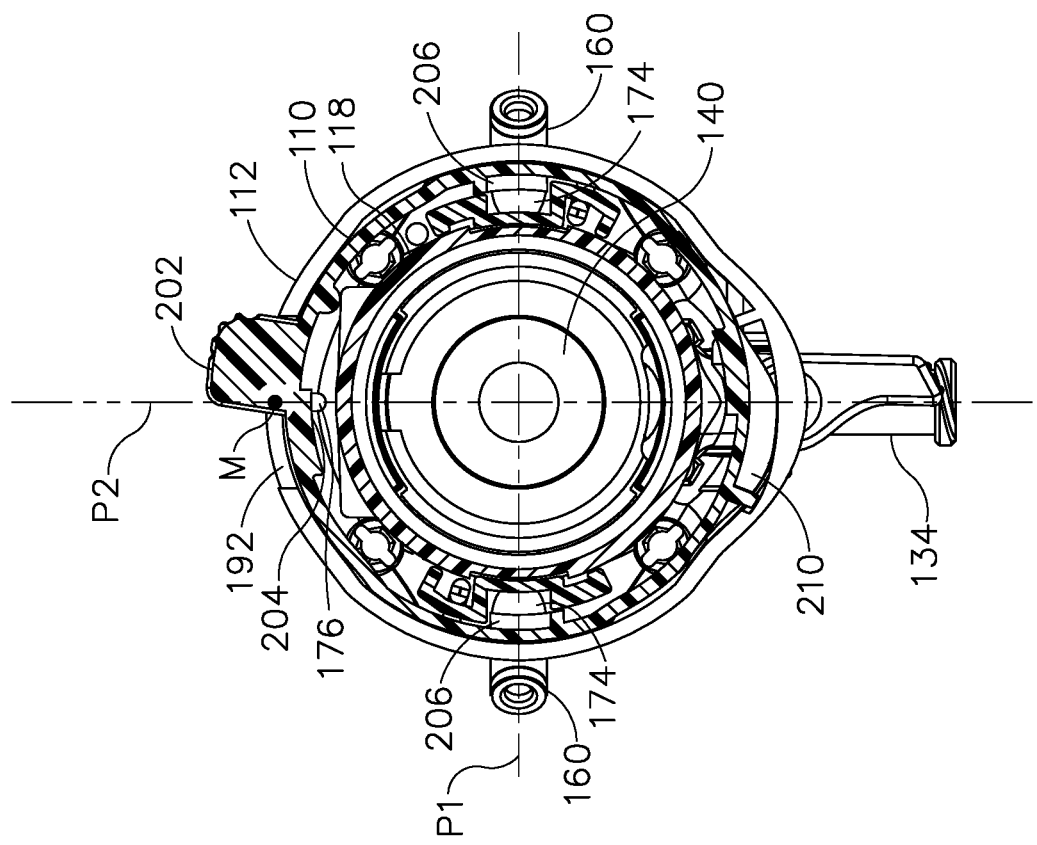

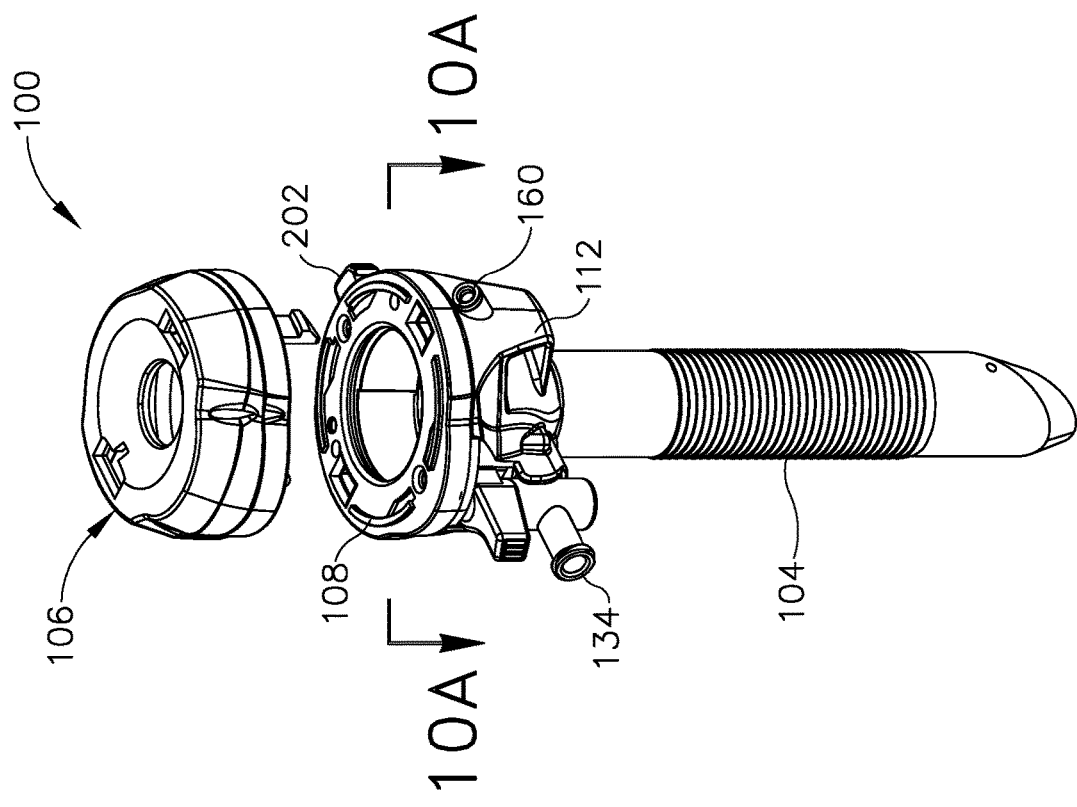
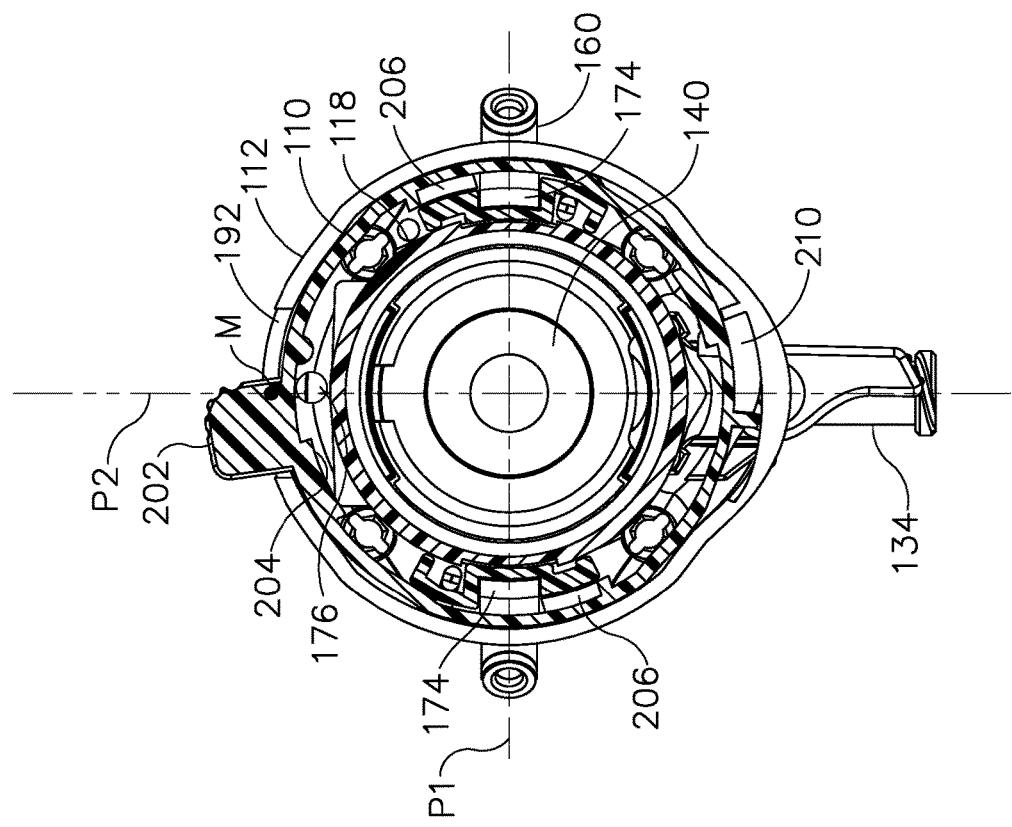
Fig.10B
Fig.10A

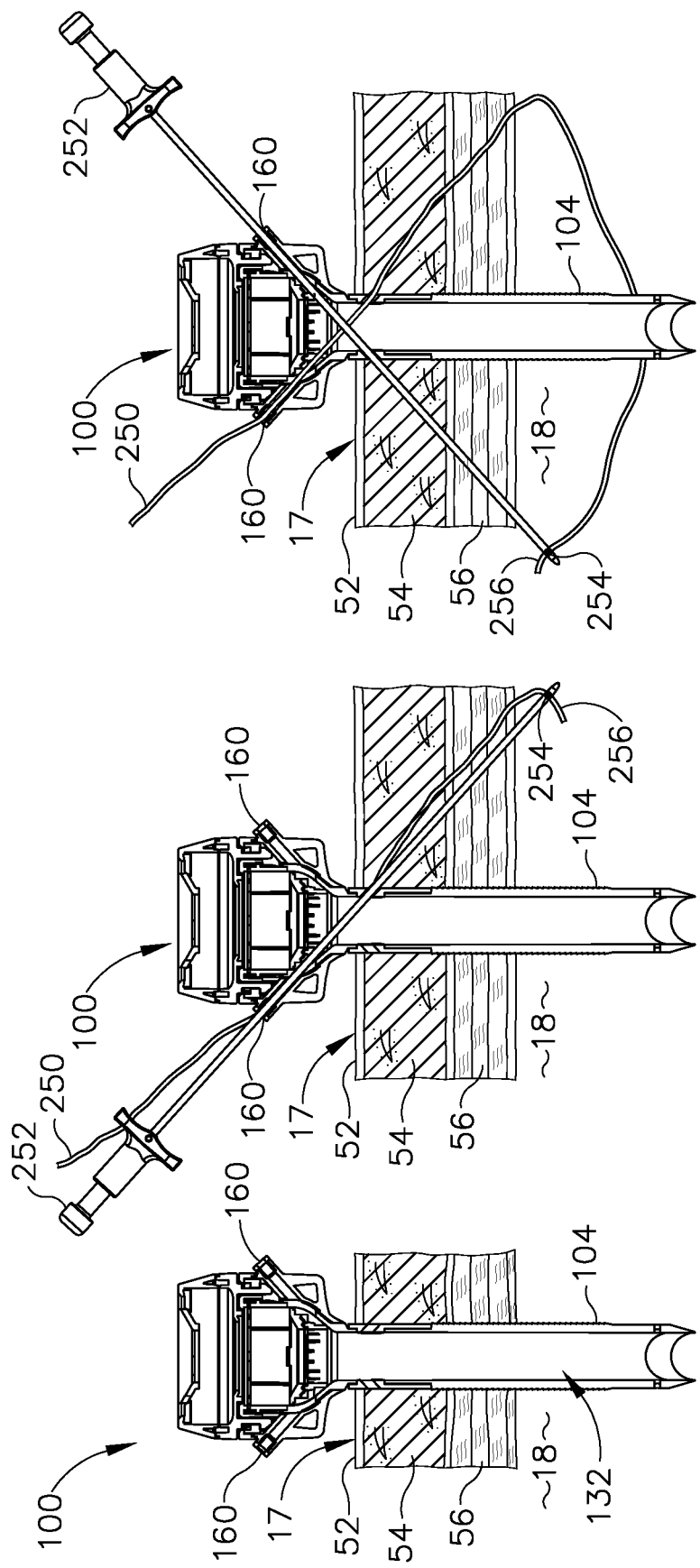

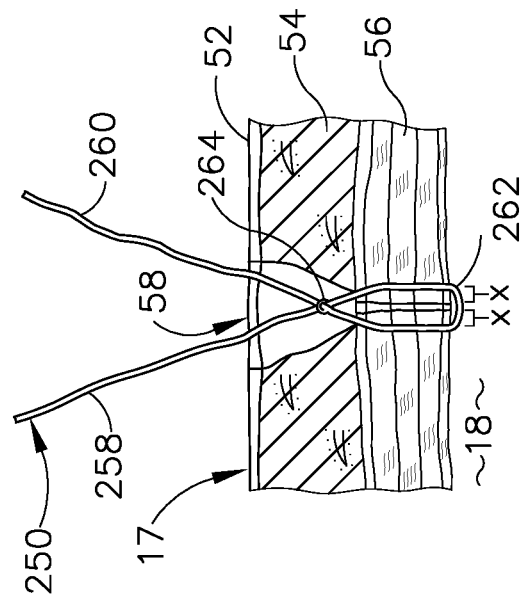
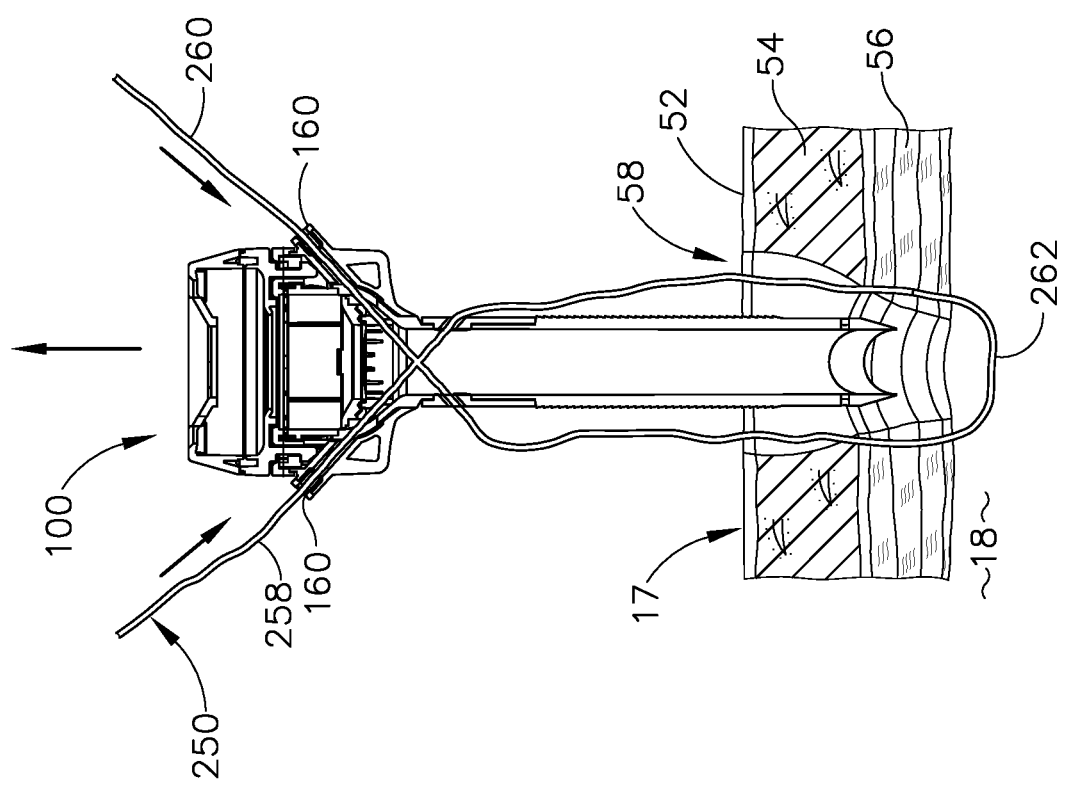

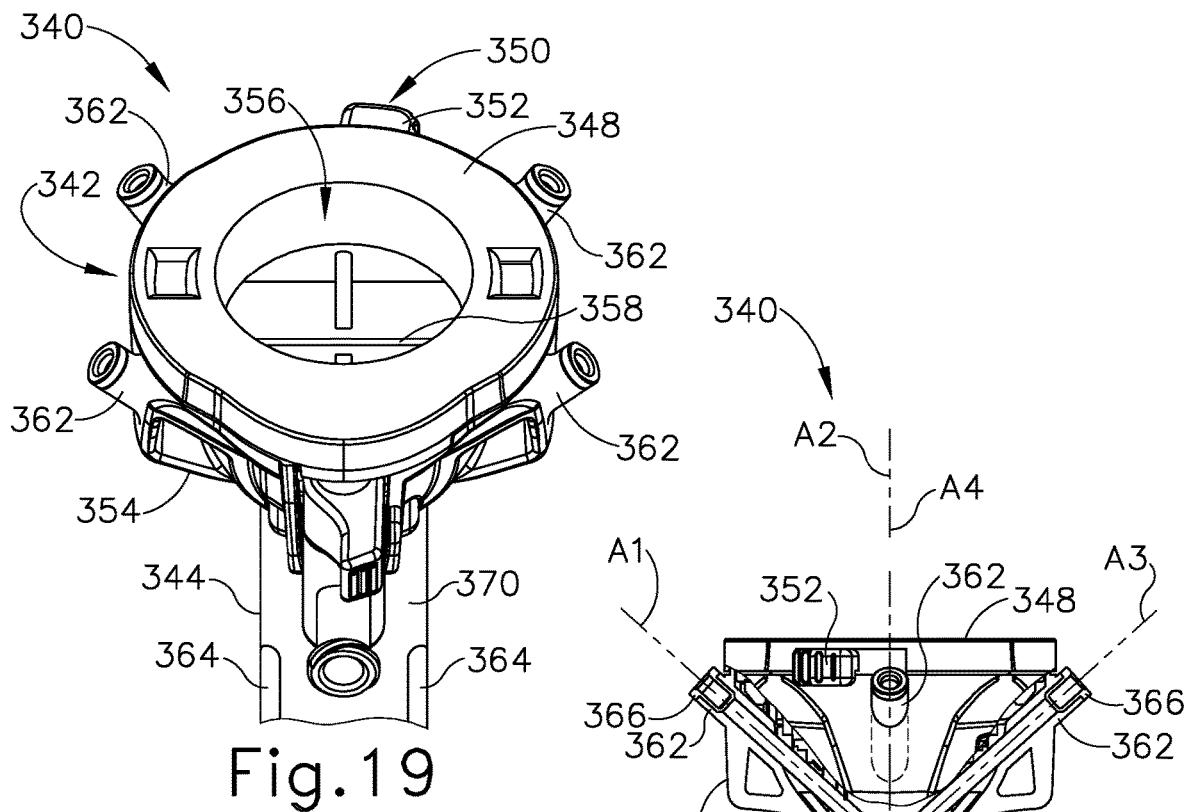
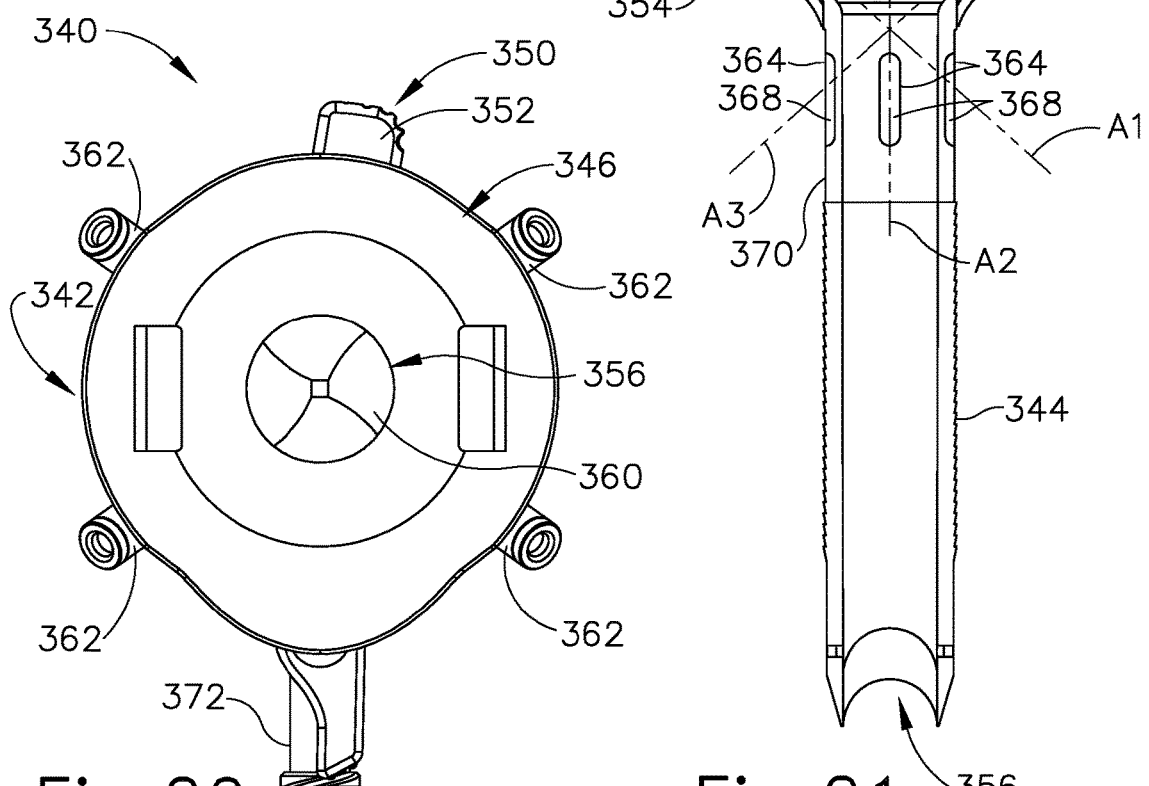
Fig.19
Fig.20
Fig.21

TROCAR WITH OBLIQUE NEEDLE INSERTION PORT AND PERPENDICULAR SEAL LATCH

BACKGROUND

Surgical procedures may require a clinician to gain access to a cavity or other desirable surgical site within a body of a patient. To perform such a surgical procedure, an incision may be made through a tissue of the patient into the cavity. Some conventional surgical procedures may apply a knife, such as a scalpel, to the tissue for the incision, while some less invasive surgical procedures, such as laparoscopic and endoscopic surgical procedures, may access the cavity through a trocar assembly. Traditional trocar assemblies generally include a trocar obturator received within a trocar cannula. In use, the clinician directs the trocar obturator and the cannula through the tissue in order to access the cavity of the desirable surgical site. Once accessed, the clinician withdraws the trocar obturator from the trocar cannula so that the trocar cannula may be used to introduce surgical instruments into the cavity for treatment.

Examples of trocar assemblies, components thereof, and other varieties of surgical access devices and wound closure devices are provided for in U.S. Pat. No. 7,981,092, entitled "Vibratory Trocar," issued Jul. 19, 2011; U.S. Pat. No. 8,226,553, entitled "Access Device with Insert," issued on Jul. 24, 2012; U.S. Pat. No. 8,251,900, entitled "Surgical Access Devices and Methods Providing Seal Movement in Predefined Paths," issued on Aug. 28, 2012; U.S. Pat. No. 8,579,807, entitled "Absorbing Fluids in a Surgical Access Device," issued on Nov. 12, 2013; U.S. Pat. No. 8,568,362, entitled "Surgical Access Device with Sorbents," issued on Oct. 29, 2013; U.S. Pat. No. 8,636,686, entitled "Surgical Access Device," issued on Jan. 28, 2014; U.S. Pat. No. 8,690,831, entitled "Gas Jet Fluid Removal in a Trocar," issued on Apr. 8, 2014; U.S. Pat. Pub. No. 2008/0200950, entitled "Surgical Hook," published on Aug. 21, 2008, now abandoned; U.S. Pat. Pub. No. 2015/0038793, entitled "Devices, Systems, and Methods for Providing Surgical Access and Facilitating Closure of Surgical Access Openings," published on Feb. 5, 2015, issued as U.S. Pat. No. 10,258,324 on Apr. 16, 2019; U.S. Pat Pub. No. 2015/0038994, entitled "Devices, Systems, and Methods for Providing Surgical Access and Facilitating Closure of Surgical Access Openings," published on Feb. 5, 2015, issued as U.S. Pat. No. 9,700,303 on Jul. 11, 2017; and U.S. Pat. Pub. No. 2015/0094741, entitled "Wound Closure Device including Mesh Barrier," published on Apr. 2, 2015 and issued as U.S. Pat. No. 9,687,226 on Jun. 27, 2017. The disclosure of each of the above-cited U.S. Patents and Publications is incorporated by reference herein.

Surgical instruments for use with such surgical access devices may have a distal end effector for engaging tissue through the access device in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Laparoscopic and endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the cavity of the patient. Positioning of an end effector may be further facilitated through inclusion of one or more articulation joints or features, enabling the end effector to be selectively articulated or otherwise deflected relative to the longitudinal axis of the shaft.

While various kinds of surgical instruments, including surgical access devices and end effectors, and other associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 4A depicts another side sectional view of the tissue shown in FIGS. 3A-3D following removal of the trocar assembly of FIG. 1, with an opening through the tissue and a suture thread being introduced into a portion of the tissue for suturing the opening closed;

FIG. 4B depicts a side sectional view of the tissue of FIG. 4A, with the suture thread being introduced though another portion of the tissue and pulled through the tissue;

FIG. 4C depicts a s side sectional view of the tissue of FIG. 4A, with the suture thread tightened and knotted for at least partially closing the opening;

FIG. 4D depicts a side sectional view of the tissue of FIG. 4A, with additional suturing for further closing the opening;

FIG. 9A depicts a top sectional view of the trocar of FIG. 5A, taken along section line 9A-9A shown in FIG. 9B, showing a latch ring of the trocar housing in a first exemplary rotational position;

FIG. 9B depicts a front perspective view of the trocar of FIG. 5A, showing a proximal housing of the trocar housing in a coupled state corresponding to the latch ring rotational position of FIG. 9A;

FIG. 10A depicts a top sectional view of the trocar of FIG. 5A, taken along section line 10A-10A shown in FIG. 10B, showing the latch ring in a second exemplary rotational position;

FIG. 10B depicts a front perspective view of the trocar of FIG. 5A, showing the proximal housing in a decoupled state corresponding to the latch ring rotational position of FIG. 9A;

FIG. 15A depicts a schematic side sectional view of tissue of a patient and the trocar of FIG. 5A positioned through an opening formed in the tissue such that the cannula extends distally into a cavity of the patient, according to a first step of an exemplary suturing procedure;

FIG. 15B depicts a schematic side sectional view of the tissue and trocar of FIG. 15A, showing completion of an exemplary second step of the suturing procedure in which a suture thread end is directed by a suture passer device distally through the trocar and fascia layers of the tissue into the cavity along a first oblique suture path;

FIG. 15C depicts a schematic side sectional view of the tissue and trocar of FIG. 15A, showing completion of an exemplary third step of the suturing procedure in which the suture passer device is re-inserted distally through the trocar and the tissue fascia layers along a second oblique suture path to capture the free suture thread end located within the cavity;

FIG. 15D depicts a schematic side sectional view of the tissue and trocar of FIG. 15A, showing completion of an exemplary fourth step of the suturing procedure in which the suture passer device and suture thread end are removed proximally such that the suture thread passes through two portions of the tissue fascia layers and proximally through the trocar, and the trocar is removed proximally from the tissue opening;

FIG. 15E depicts a schematic side sectional view of the tissue and trocar of FIG. 15A, showing completion of an exemplary fifth step of the suturing procedure in which the suture thread is pulled and knotted to draw together the tissue fascia layers;

FIG. 19 depicts a top perspective view of another exemplary trocar having four circumferentially spaced needle guide structures and corresponding needle ports;

FIG. 20 depicts a top elevational view of the trocar of FIG. 19; and

FIG. 21 depicts a side elevational view of the trocar of FIG. 19, showing suture paths extending through the needle guide structures and the corresponding needle ports.

Figure 1:
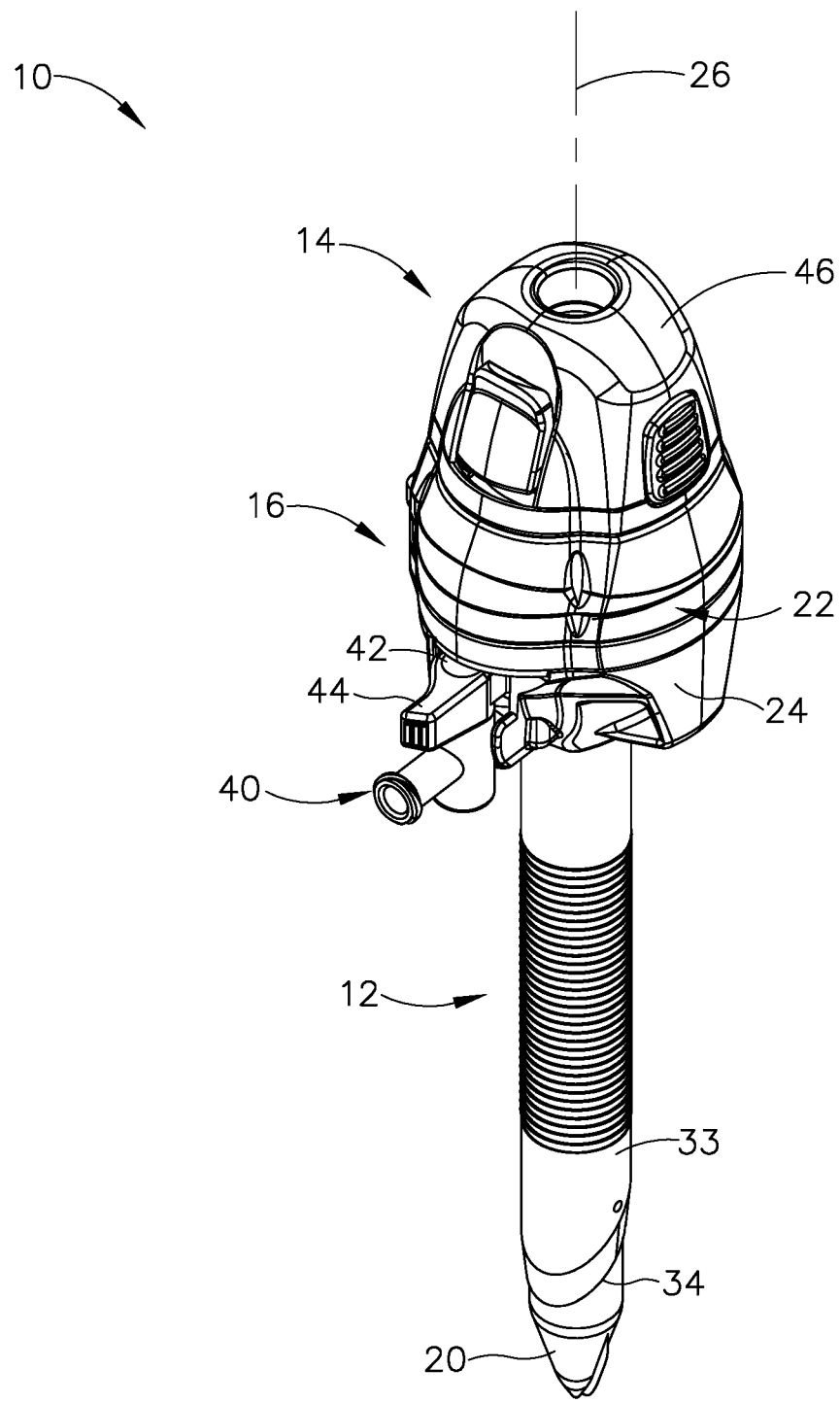
FIG. 1 depicts a perspective view of an exemplary trocar assembly.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Access Device

Figure 2:
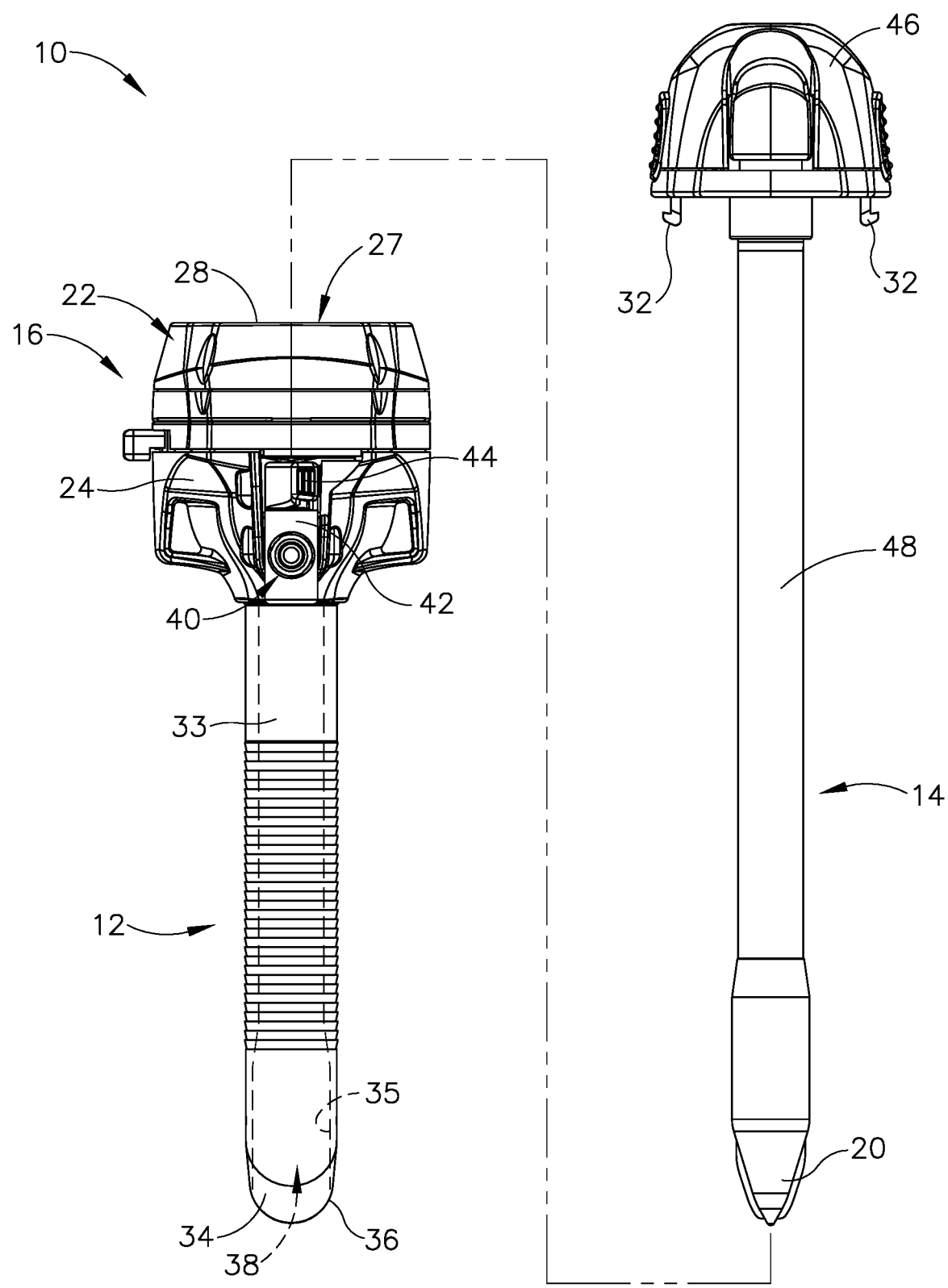
FIG. 2 depicts a partially exploded side elevational view of the trocar assembly of FIG. 1 having a trocar housing, a trocar cannula, and an obturator.

FIGS. 1-2 depict an exemplary surgical access device in the form of a first exemplary trocar assembly (10) that includes a trocar cannula (12) and a trocar obturator (14). Trocar obturator (14) is removably received within trocar cannula (12) through a trocar housing (16) of trocar cannula (12). As shown in FIG. 1 with trocar obturator (14) positioned within trocar cannula (12), a clinician inserts trocar assembly (12) through tissue (17) (see FIG. 3A) of a patient at a desirable surgical site for accessing a cavity (18) (see FIG. 3A) within the patient. By way of example only, trocar assembly (10) may be inserted in a patient's abdomen, between two of the patient's ribs, or elsewhere. A tip (20) of trocar obturator (14) projects distally from trocar cannula (12) to puncture tissue (17) (see FIG. 3A) for introducing a distal end portion of trocar cannula (12) into cavity (18) (see FIG. 3B). The clinician proximally withdraws trocar obturator (14) from trocar cannula (12) such that cavity (18) (see FIG. 3C) within the patient is in communication with a surgical environment via trocar cannula (12). The clinician may then introduce a fluid, such as a gas, through trocar cannula (12) for inflating cavity (18) (see FIG. 3A) and/or an end effector of a surgical instrument through trocar cannula (12) for engaging tissue (17) to achieve a diagnostic or therapeutic effect.

It should be understood that terms such as "proximal" and "distal" are used herein with reference to the clinician gripping trocar housing (16). Thus, tip (20) is distal with respect to the more proximal trocar housing (16). It will be further appreciated that for convenience and clarity, spatial terms such as "vertical" and "horizontal" are used herein with respect to the drawings. However, surgical instruments are used in many orientations and positions, and these terms are not intended to be limiting and absolute. Further, in some instances, components are referred to interchangeably with and without the term "assembly," e.g., a trocar and a trocar assembly. There is no particular intention for the terms to refer to different components. Likewise, terms such as "instrument" and "device" may be used interchangeably.

A. Exemplary Trocar Assembly with Cannula and Obturator

Trocar assembly (10) of FIGS. 1-2 includes cannula (12) extending distally from trocar housing (16). In the present example, trocar housing (16) has a generally cylindrical shape with a proximal removable cap (22) atop a distal housing chamber (not shown). Cap (22) is selectively attachable and detachable from housing chamber (not shown). Trocar housing (16) includes a housing sidewall (24) that extends circumferentially around a central longitudinal axis (26) through trocar assembly (10), and thus along trocar cannula (12). Trocar housing (16) further includes a central lumen (27) extending from a proximal housing end opening (28) to a distal housing end opening (not shown). As shown, cap (22) selectively mates with housing sidewall (24) via distal mating members (not shown) and further includes proximal mating members, such as slots (not shown), configured to removably connect to a pair of tabs (32), respectively, that extend distally from a portion of obturator (14). However, it will be appreciated that alternative structures and devices may also be removably connected to cap (22) during use.

Cannula (12) extends distally from trocar housing (16), and is also generally defined by a cannula sidewall (33) extending circumferentially around central longitudinal axis (26). Cannula sidewall (33) extends distally to a beveled end (34) such that cannula sidewall (33) and beveled end (34) are configured to be inserted through tissue (17) (see FIG. 3A) as discussed below in greater detail for accessing cavity (18) (see FIG. 3A). To this end, cannula (12) generally has a smaller diameter than trocar housing (16), which is configured to remain exterior of tissue (17) (see FIG. 3C). In addition, cannula (12) defines an interior lumen (35) with a proximal cannula end opening (not shown) and a distal cannula end opening (36), which extends through beveled end (34). In the present example, distal housing end opening (not shown) of trocar housing (16) fluidly connects to proximal cannula end opening (not shown) such that central lumen (27) of trocar housing (16) and interior lumen (35) of cannula (12) define a working channel (38). Working channel (38) thus extends from proximal housing end opening (28) to distal cannula end opening (36) and is configured to receive one or more surgical instruments therethrough for accessing cavity (18).

Furthermore, an insufflation port (40) is operatively connected to trocar housing (16) to control the flow of an insufflation fluid, such as carbon dioxide, through a portion of cannula (12) and into cavity (18). More particularly, insufflation port (40) includes a stopcock valve (42) and a cock valve lever (44), which can work together to allow and/or prevent passage of the insufflation fluid into tubing (not shown), through trocar housing (16), and into trocar cannula (12). Trocar housing (16) and cannula (12) respectively have proximal and distal seal assemblies (not shown) positioned within central lumen (27) and interior lumen (35) of working channel (38). In the present example, the proximal seal assembly is an instrument seal (not shown), whereas the distal seal assembly (not shown) is a zero-closure seal, such as a duckbill seal (not shown). Instrument seal (not shown) is retained within cap (22) and is configured to fluidly seal against a surgical instrument extending through working channel (38). In contrast, duckbill seal (not shown) is configured to form a seal in working channel (38) when no instrument is disposed therethrough to thereby inhibit the leakage of insufflation fluid during use. Of course, it will be appreciated that alternative seal assemblies may be positioned within working channel (38) for inhibiting such leakage of insufflation fluid.

Duckbill seal is further configured to be manipulated to provide an opening to working channel (38) that is larger than a corresponding opening provided by instrument seal. This larger opening provided by duckbill seal may facilitate extraction of bodily tissue through trocar housing (16) during a surgical procedure. In particular, cap (22) may be removed, and proximal instrument seal along with it, to expose the duckbill seal and thereby enable a surgeon to extract bodily tissue proximally through the duckbill seal opening that would otherwise be too large to extract proximally through the instrument seal opening.

As discussed briefly above, obturator (14) is used in conjunction with cannula (12) for inserting trocar assembly (10) into the patient. Obturator (14) of the present example, includes a handle head (46) with a cylindrical shaft (48) extending distally therefrom to tip (20), which is generally configured to puncture tissue (17) (see FIG. 3A) as described below in greater detail. Handle head (46) is configured to be gripped by the clinician during use and includes selectively movable tabs (32) extending distally to removably connect with trocar housing (16) for selective securement. Shaft (48) is received through working channel (38) such that tip (20) extends distally from beveled end (34). Of course, obturator (14) may be selectively removed from cannula (12) and trocar housing (16) to free working channel (38) for use. While the present example of trocar assembly (10) has obturator (14), it will be appreciated that cannula (12) may be inserted in some examples without obturator (14) or may be alternatively configured to aid insertion without using obturator (14).

B. Exemplary Method of Accessing a Cavity within a Patient

Figure 3A:
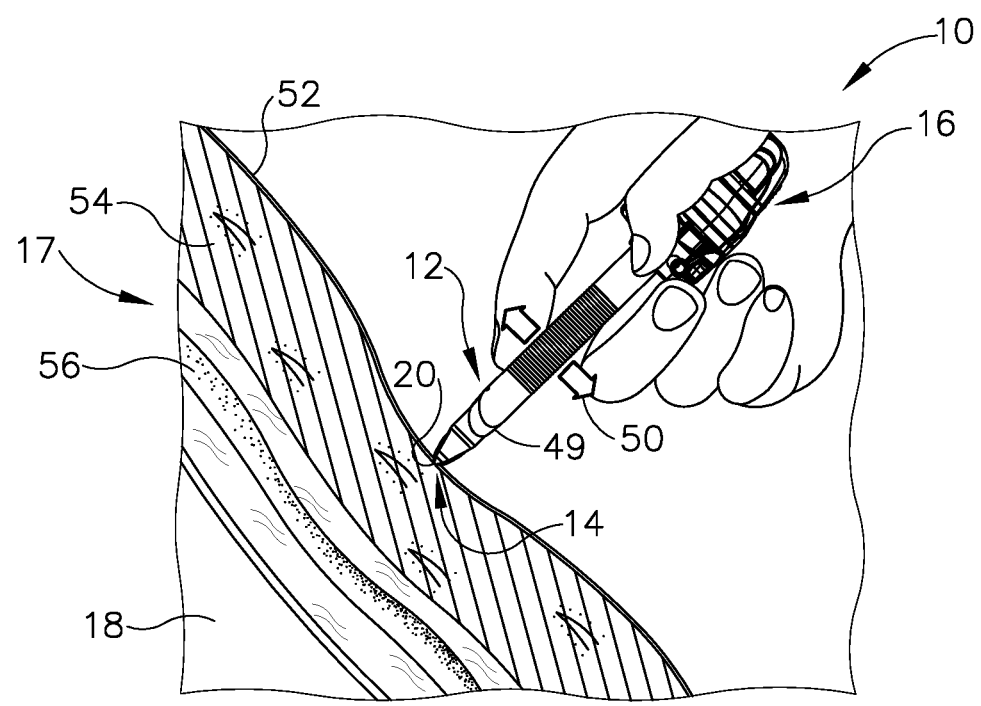
FIG. 3A depicts a side sectional view of tissue of a patient with the trocar assembly of FIG. 1 being manipulated by a clinician through the tissue.
Figure 3B:
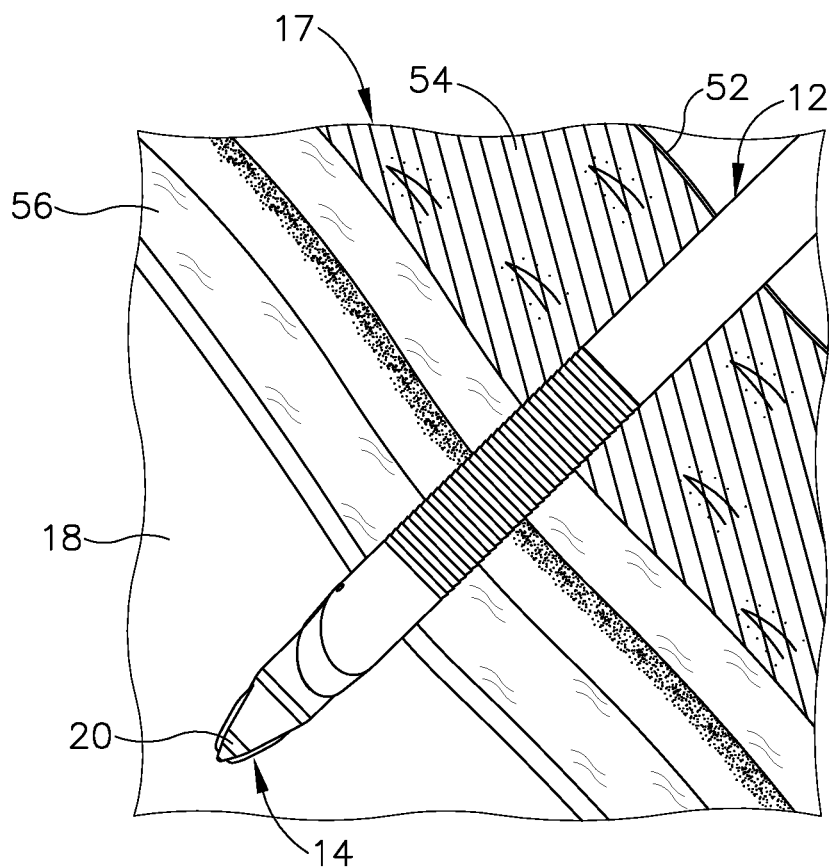
FIG. 3B depicts a side sectional view of the tissue and trocar assembly of FIG. 3A, with the trocar assembly of FIG. 1 inserted through the tissue and received within a cavity of the patient.
Figure 3C:
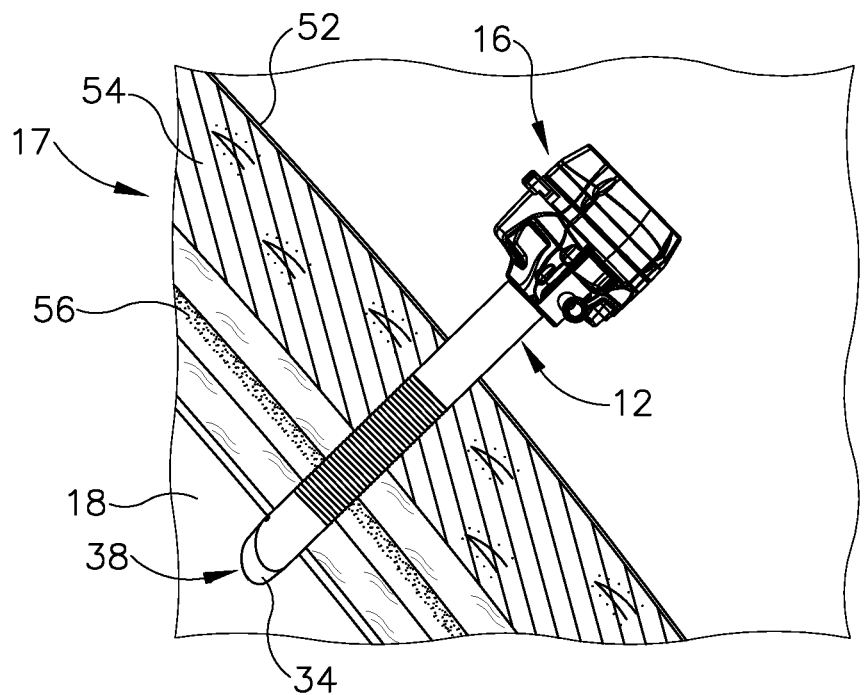
FIG. 3C depicts a side sectional view of the tissue and the trocar assembly of FIG. 3A, with the obturator withdrawn from the trocar cannula for accessing the cavity via a working channel through the trocar cannula and the trocar housing.
Figure 3D:
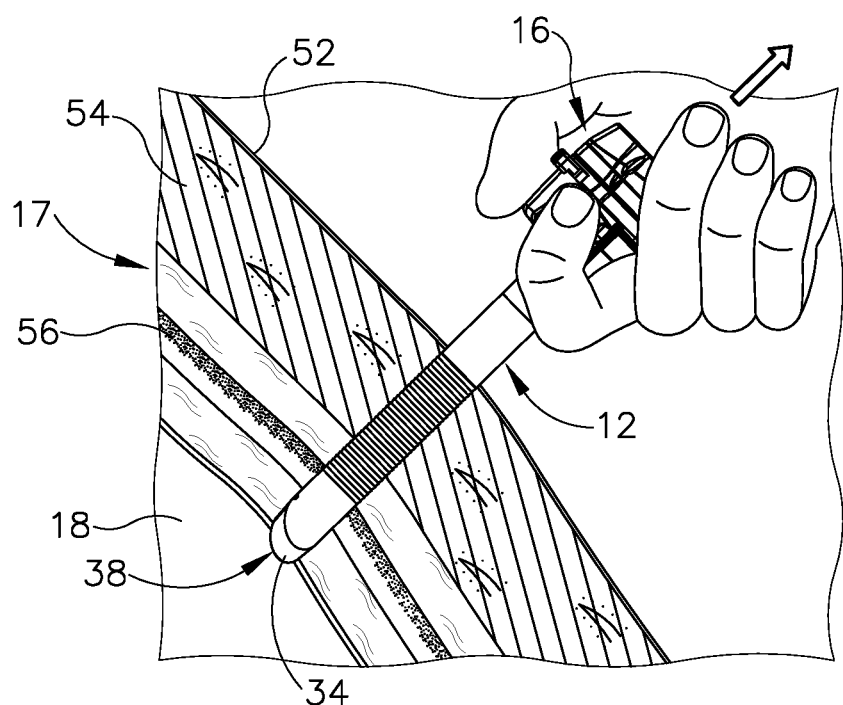
FIG. 3D depicts a side sectional view of the tissue and the trocar assembly of FIG. 3C, with the trocar housing and the trocar cannula being removed from the cavity and the tissue of the patient.

FIGS. 3A-3D illustrate accessing cavity (18) through tissue (17) with trocar assembly (10) discussed above. Tissue (17) of the present example more particularly has relatively outward superficial layers and relatively inward deep layers. Superficial layers generally include an outer layer of skin (52) and an inner layer of fat (54); whereas the deeper layers include layers of fascia (56), which are fibrous and flexible with relatively higher tensile strength than the superficial layers. As shown in FIG. 3A, with obturator (14) received within cannula (12) and connected to trocar housing (16), the clinician manipulates trocar assembly (10) to urge tip (20) of obturator (14) against skin (52) and inward toward cavity (18) while rotating trocar assembly (10) back and forth. Arrow (49) and arrow (50) respectively indicate this inward and rotatable movement. Continued inward urging of trocar assembly (10) further directs tip (20) and beveled end (34) of cannula (12) through the layers of fat (54) and fascia (56) and into cavity (18) as shown in FIG. 3B. The clinician then disconnects obturator (14) from trocar housing (16) and withdraws obturator (14) from cannula (12) to establish access from the exterior of tissue (17) into cavity (18) via working channel (38) as shown in FIG. 3C for achieving a diagnostic or therapeutic effect with another surgical instrument (not shown). Once the diagnostic or therapeutic effect is complete, clinician withdraws cannula (12) and trocar housing (16) outwardly for removal from tissue (17) as shown in FIG. 3D.

As shown in FIG. 4A, removal of cannula (12) from tissue (17) generally results in a tissue opening (58), which may also be referred to as a tissue port or tissue wound, that clinician closes to encourage healing of tissue (17). While some tissue openings may sufficiently close as tissue (17) comes together, other openings, such as tissue opening (58), are sutured closed with a suture thread (60). In one example shown in FIGS. 4A-4D, suture thread (60) is removably coupled with a needle (62) for guiding suture thread (62) through tissue (17) as the clinician manipulates needle (62). More particularly, as shown in FIG. 4B, the clinician directs needle (62) downwardly through fascia (56) on one side of tissue opening (58) and then upwardly through fascia (56) on the other side of tissue opening (58) as needle (62) clears tissue (17). Notably, the clinician threads needle (62) though fascia (56) a desirable distance distally from tissue opening (58) in order to provide a relatively close proximity to tissue opening (58); but also at a sufficient distance to provide ample fascia (56) for anchoring suture thread (60) therein. Additionally, the clinician angles a tip of needle (62) obliquely away from a central axis of opening (58) at a suitable angle in order to achieve sufficient "bite" when anchoring suture thread (60) within fascia (56). As shown in FIG. 4C, suture thread (60) from respective sides of tissue opening (58) are brought together and pulled to similarly pull tissue (17) together and at least partially close tissue opening (58). The clinician then knots suture thread (60) to secure tissue (17) together and sufficiently close tissue opening (58) with a formed suture (64) as shown in FIG. 4D. Additional sutures (64) may be placed along tissue (17) to further close tissue opening (58) and encourage healing of tissue (17).

While the above described suturing technique shown in FIGS. 4A-4D is one exemplary procedure for closing tissue opening (58) with suture thread (60) following use of trocar assembly (10) (see FIG. 1), other exemplary procedures and devices may be alternatively used for closing such tissue openings. By way of example, U.S. patent application Ser. No. 15/088,723, entitled "Surgical Access Devices with Integrated Wound Closure Features," filed Apr. 1, 2016, published as U.S. Pat. Pub. No. 2017/0281154 on Oct. 5, 2017, issued as U.S. Pat. No. 10,299,785 on May 28, 2019, which is incorporated by reference herein in its entirety, describes an alternative trocar assembly and suturing technique. To this end, alternative trocar assemblies and suturing techniques may be used in any combination as desired by the clinician.

II. Exemplary Surgical Access Device Having Wound Closure Features

Figure 5A:
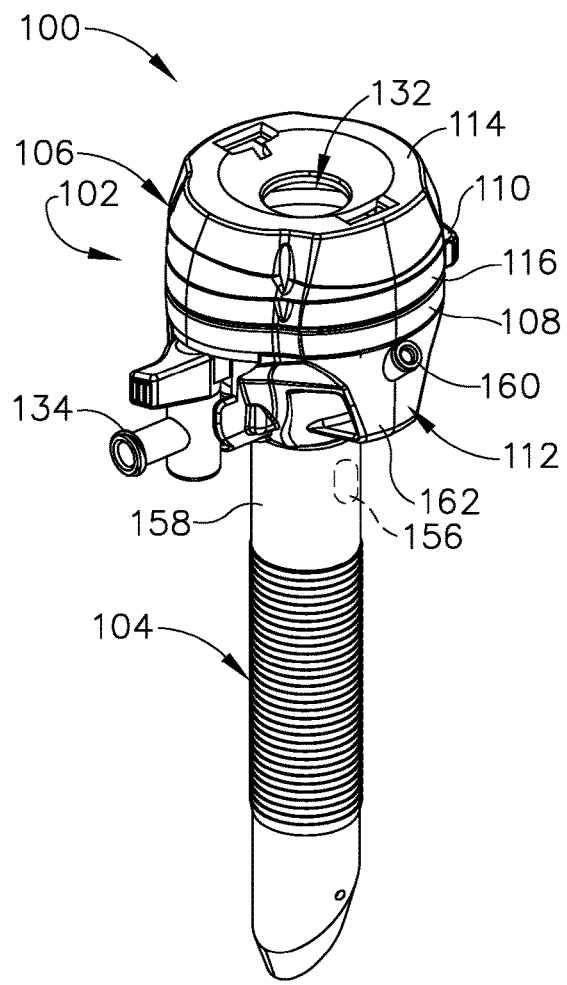
FIG. 5A depicts a front perspective view of an exemplary trocar having a housing and a cannula.
Figure 5B:
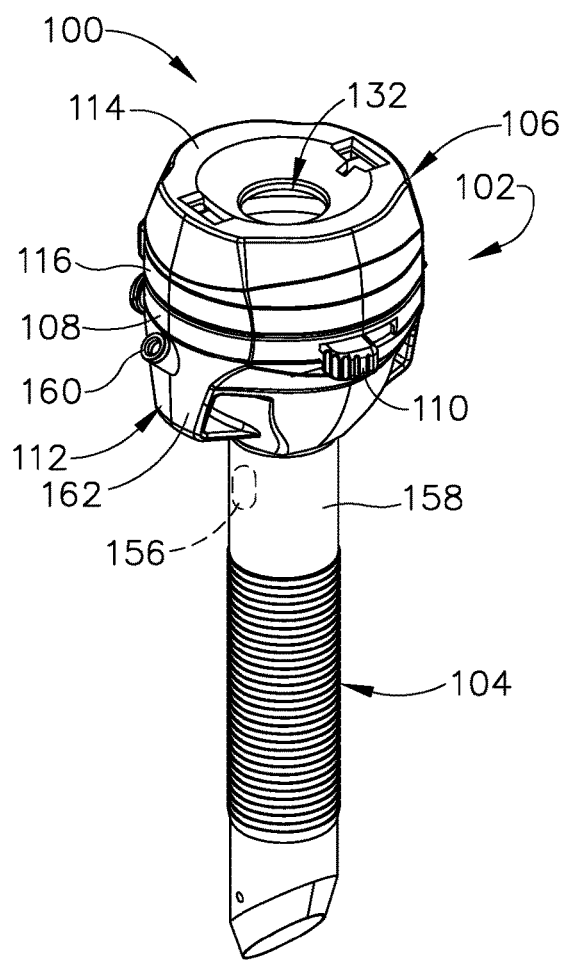
FIG. 5B depicts a rear perspective view of the trocar of FIG. 5A.
Figure 6:
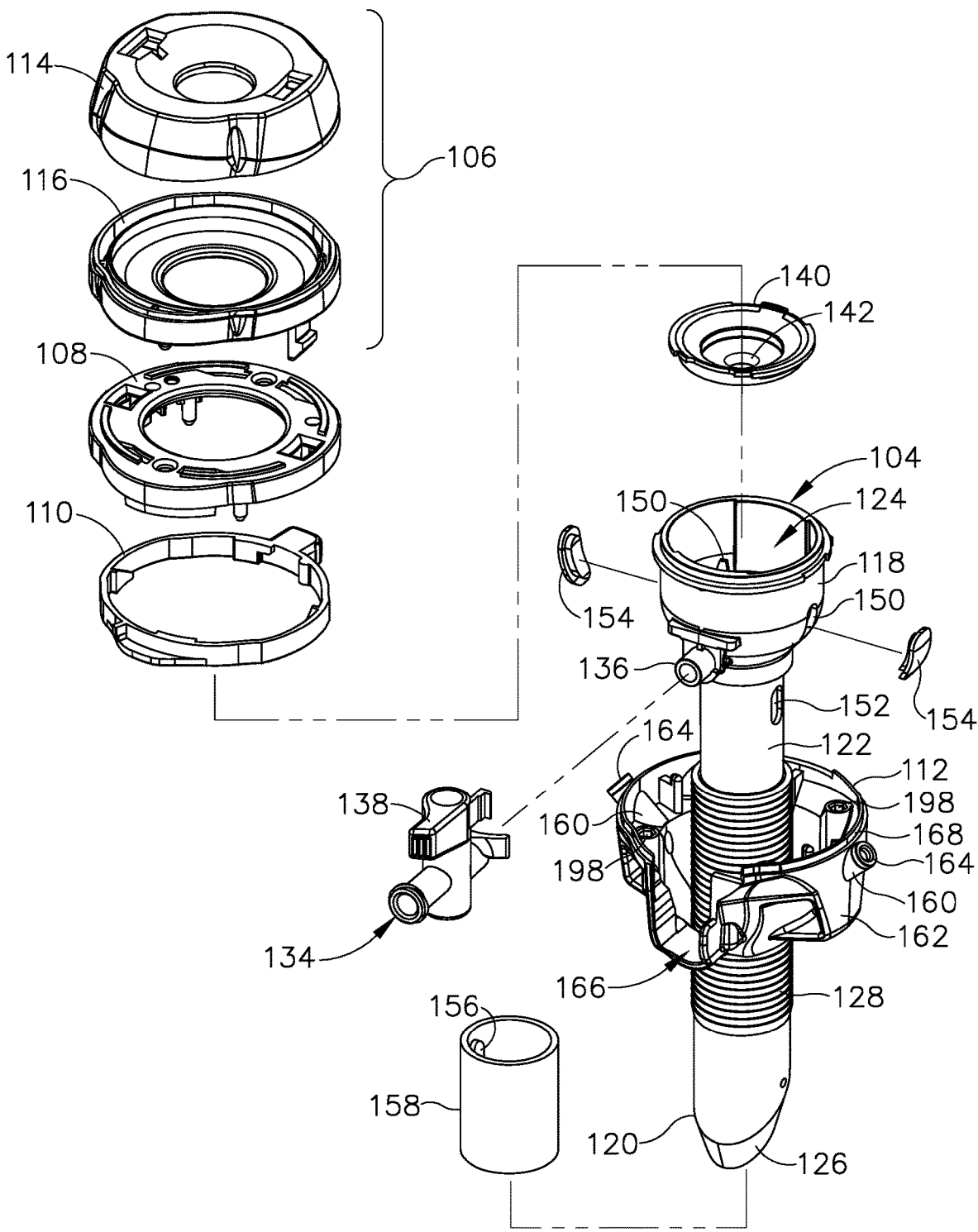
FIG. 6 depicts an exploded perspective view of the trocar of FIG. 5A.

A. Exemplary Trocar Having Latch Ring and Needle Ports Defining Oblique Suture Paths FIGS. 5A-6 show another exemplary surgical access device in the form of a trocar (100). Though not shown, those of ordinary skill in the art will recognize that trocar (100) may be used in combination with any suitable trocar obturator, such as obturator (14) described above, for example. Trocar (100) generally includes a housing (102) and a cannula (104) coupled to and extending distally from housing (102) along a central longitudinal axis of trocar (100). Housing (102) includes a proximal housing (106), a housing cap plate (108), a latch member such as a latch ring (110), and a distal housing (112). Proximal housing (106) has a proximal housing head (114) and a proximal housing base (116). As described in greater detail below, proximal housing (106) is coupled with and selectively releasable from the remainder of trocar (100) via housing cap plate (108) and latch ring (110). In particular, distally extending protrusions of proximal housing (106) are received through housing cap plate (108) and are releasably engaged by latch ring (110). Latch ring (110) is rotatable about a central axis of trocar (100) to selectively release the distally extending protrusions and thereby enable separation of proximal housing (102) proximally from housing cap plate (108). As described below, latch ring (110) is suitably oriented to avoid obstructing needle ports and needle guide tubes that define suture paths extending obliquely through trocar (100).

As shown in FIG. 6, cannula (104) includes a proximal hub (118), a distal tip (120), and a cylindrical body (122) extending therebetween along the central axis of trocar (100). Proximal hub (118) flares radially outwardly from cylindrical body (122) in a proximal direction and defines a proximal opening to a cannula lumen (124), while distal tip (120) defines a distal opening to cannula lumen (124). Distal tip (120) itself is beveled and includes a chamfered edge (126) to facilitate insertion of distal tip (120) through tissue and into a patient body cavity during a surgical procedure. An outer surface of cylindrical body (122) may be provided with a plurality of tissue engagement ribs (128) or other similar features suitable to frictionally engage the inner wall of a tissue opening through which cannula (104) is received into the body cavity.

Figure 11:
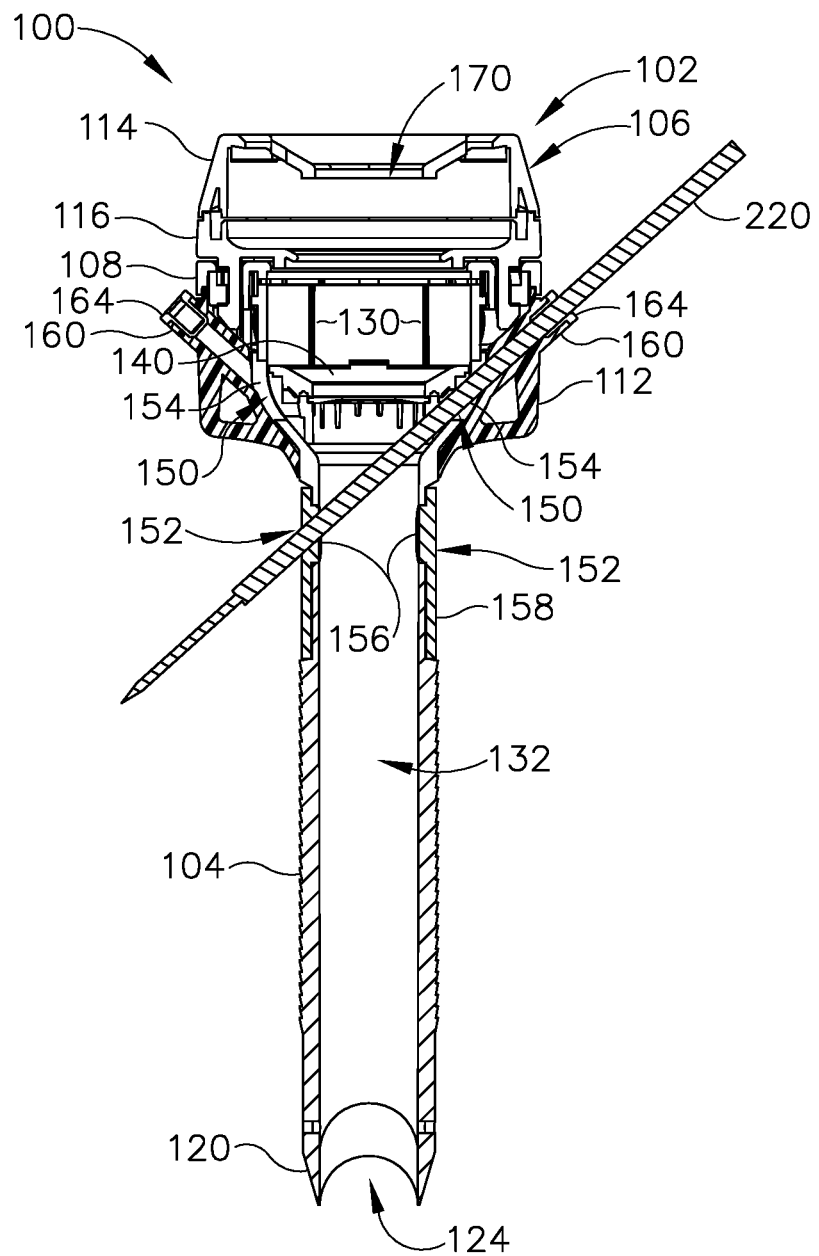
FIG. 11 depicts a side sectional view of the trocar of FIG. 5A, showing an exemplary suture needle passer extending through the trocar along a first suture path oriented obliquely relative to a central axis of the trocar.

Referring briefly to FIG. 11, cannula lumen (124) fluidly communicates with an interior (130) of housing (102) to collectively define a working channel (132) extending through trocar (100) along the central axis thereof. A distal opening to working channel (132) is defined by distal tip (120) of cannula (104), and a proximal opening to working channel (132) is defined by proximal housing head (114). In configurations in which proximal housing (106) is decoupled from the remainder of trocar (100), for example as described below with reference to FIG. 10B, the proximal opening to working channel (132) is defined by housing cap plate (108). Working channel (132) is configured to receive one or more surgical instruments therethrough, such as a variety of endoscopic surgical instruments for example, for accessing the patient body cavity and observing and/or treating tissue accessible therein.

As shown in FIG. 6, an insufflation port (134) (or "stopcock") is operatively connected to proximal hub (118) of cannula (104) at fitting (136), and includes an internal valve (not shown) similar to valve (42) and a valve lever (138). Insufflation port (134) may be formed integrally with fitting (136), or alternatively coupled to fitting (136) during assembly of trocar (100). Insufflation tubing (not shown) is coupled to an inlet of insufflation port (134) and directs insufflation fluid, such as carbon monoxide, from a fluid source into insufflation port (134), which directs the fluid distally through working channel (132) into the patient body cavity. Valve lever (138) is configured to rotate the internal valve (not shown) between open and closed positions to control the flow of insufflation fluid through insufflation port (134).

Similar to trocar assembly (10), trocar (100) may include a proximal (or "outer") seal assembly and/or a distal (or "inner") seal assembly each arranged within working channel (132). In the present example, trocar (100) includes a distal seal assembly in the form of an instrument seal (140) arranged within a distal tapered portion of proximal hub (118). Distal instrument seal (140) includes a central opening (142) configured to receive a surgical instrument therethrough, and is configured to sealingly engage an outer surface of a surgical instrument extending through central opening (142) to prevent proximal advancement of bodily fluids and/or tissue into interior (130) of housing (102). In exemplary configurations, instrument seal (140) may be configured to absorb or otherwise remove bodily fluids from the outer surface of the surgical instrument as the surgical instrument is retracted proximally through instrument seal (140). Though not shown, trocar (100) may further include a proximal seal assembly arranged within proximal housing (106).

Those of ordinary skill in the art will recognize that trocar (100) may include proximal and/or distal seal assemblies of various alternative configurations, such as those disclosed in U.S. patent application Ser. No. 15/088,723, published as U.S. Pat. Pub. No. 2017/0281154, issued as U.S. Pat. No. 10,299,785 on May 28, 2019, incorporated by reference above. For instance, though not shown, trocar (100) may include a proximal seal assembly in the form of an instrument seal arranged within proximal housing (106), and a distal seal assembly in the form of a zero-closure seal, such as a duckbill seal, arranged within proximal hub (118) of cannula (104). As described above with reference to trocar assembly (10), such a zero-closure seal is generally configured to form a fluid-tight seal in working channel (132) and thereby maintain insufflation even when no surgical instrument is present in working channel (132). Furthermore, the distal zero-closure seal may be manipulated to provide an opening to a distal portion of working channel (132) (e.g., cannula lumen (124)) that is large enough to enable extraction of tissue proximally therethrough, particularly when proximal housing (106) is removed from trocar (100) to provide access to the distal zero-closure seal.

As shown in FIG. 6, trocar (100) further includes a plurality of needle ports formed in select side portions of cannula (104). As described in greater detail below, each needle port is configured to direct a suture passer needle (or simply "suture passer") across working channel (132) of trocar (100) at an oblique angle relative to the central axis of trocar (100) (see FIG. 11) to thereby establish an oblique suture path extending through trocar (100) and adjacent tissue. As used herein, the term "oblique" means neither parallel nor perpendicular to the referenced axis, such as the central axis of trocar (100).

In the present example, trocar (100) includes a pair of needle entrance ports (150) and a corresponding pair of needle exit ports (152) arranged distally of needle entrance ports (150). Needle entrance ports (150) extend through respective side portions of proximal hub (118) of cannula (104) at diametrically opposed positions, and open to cannula lumen (124). Needle exit ports (152) extend through respective side portions of cylindrical body (122) of cannula (104) at diametrically opposed positions, and open to cannula lumen (124). Each needle port (150, 152) is generally elongate along the central axis of trocar (100), though needle ports (150, 152) may be formed with various other shapes in alternative configurations.

Each needle entrance port (150) is configured to cooperate with an opposing needle exit port (152) to direct a suture passer needle along a respective oblique suture path. In particular, a needle entrance port (150) on a first side of cannula (104) cooperates with a needle exit port (152) on an opposing second side of cannula (104) to define a first oblique suture path. Similarly, a needle entrance port (152) on the second side of cannula (104) cooperates with a needle exit port (152) on the opposing first side of cannula (104) to define a second oblique suture path. In the present example, each needle exit port (152) is positioned in circumferential alignment with the adjacent needle entrance port (150), such that the resulting oblique suture paths define an X-shaped pattern in a single suture plane extending along the central axis of trocar (100). In other examples, needle entrance ports (150) and/or needle exit ports (152) may be arranged in a non-diametrically opposed configuration, and/or needle exit ports (152) may be circumferentially offset from needle entrance ports (150), such that the resulting oblique suture paths lie in separate suture planes.

Each needle exit port (152) may be spaced distally from its respective needle entrance port (150) by a distance suitable to achieve a desired suture path angle (or "tissue bite angle") measured between the resulting suture path and the central axis of trocar (100). In the present example, each needle exit port (152) is spaced distally from its respective needle entrance port (150) by the same axial distance, such that the resulting suture paths exhibit the same suture path angles. In other examples, however, needle exit ports (152) may be spaced distally at different distances to achieve different suture path angles. Moreover, in various other examples, any suitable quantity and arrangement of needle entrance ports (150) and needle exit ports (152) may be provided.

Each needle port (150, 152) is provided with a pierceable seal configured to aid in maintaining insufflation when a suture passer needle is directed through trocar (100) along the suture paths, and/or when the suture passer needle is withdrawn from trocar (100). In the present example, each needle entrance port (150) is provided with an entrance seal shown in the form of an elongate plug (154), and each needle exit port (152) is provided with an exit seal shown in the form of an elongate protrusion (156) projecting radially inwardly from an inner surface of a cannula sleeve (158). Each seal (154, 156) is shaped to sealingly engage its respective needle port (150, 152). As shown in FIGS. 5A-6, cannula sleeve (158) is received over a narrowed region of cylindrical body (122) of cannula (104), and has an outer diameter similar to an outer diameter of a distal region of cylindrical body (122) located distally of tissue engagement ribs (128). In exemplary configurations, plugs (154) and cannula sleeve (158), including protrusions (156), and may be formed of an elastomeric material. Additionally, cannula sleeve (158) may be overmolded over cannula (104) during manufacture.

Trocar (100) further includes a pair of needle guide structures shown in the form of guide tubes (160), each configured to guide a suture passer needle along the oblique suture path defined by the respective pair of needle entrance and exit ports (150, 152), described above. In the present example, needle guide tubes (160) are formed integrally with distal housing (112) and extend angularly through side wings (162) of distal housing (112). Each needle guide tube (160) includes a proximal opening through which a suture passer needle is introduced, and a distal opening that confronts seal plug (154) of a respective needle entrance port (150), as shown in FIG. 11. Additionally, the entrance opening of each needle guide tube (160) includes a seal cap (164). As described in greater detail below with reference to FIGS. 12A and 12B, seal caps (164) are pierceable by a suture passer needle and function in a manner similar to seal plugs (154) to assist in maintaining insufflation during a surgical procedure. While the needle guide structures of the present example are shown in the form of needle guide tubes (160), it will be appreciated that in alternative examples various other structures suitable to guide a suture passer needle along the oblique suture paths of trocar (100) may be employed instead. In other examples, such needle guide structures may be omitted from trocar (100).

As shown in FIGS. 5A-6, distal housing (112) is in the form of a generally annular shell shaped to receive and encircle proximal hub (118) of cannula (104). A sidewall of distal housing (112) includes a cutout (166) that accommodates insufflation port (134), which extends radially outwardly from proximal hub (118). As described above, distal housing (112) includes a pair of diametrically opposed side wings (162) that support needle guide tubes (160). During a surgical procedure, side wings (162) may be gripped by a surgeon when introducing trocar (100) through patient tissue. An upper edge (168) of distal housing (112) supports housing cap plate (108) and latch ring (110).

Figure 7A:
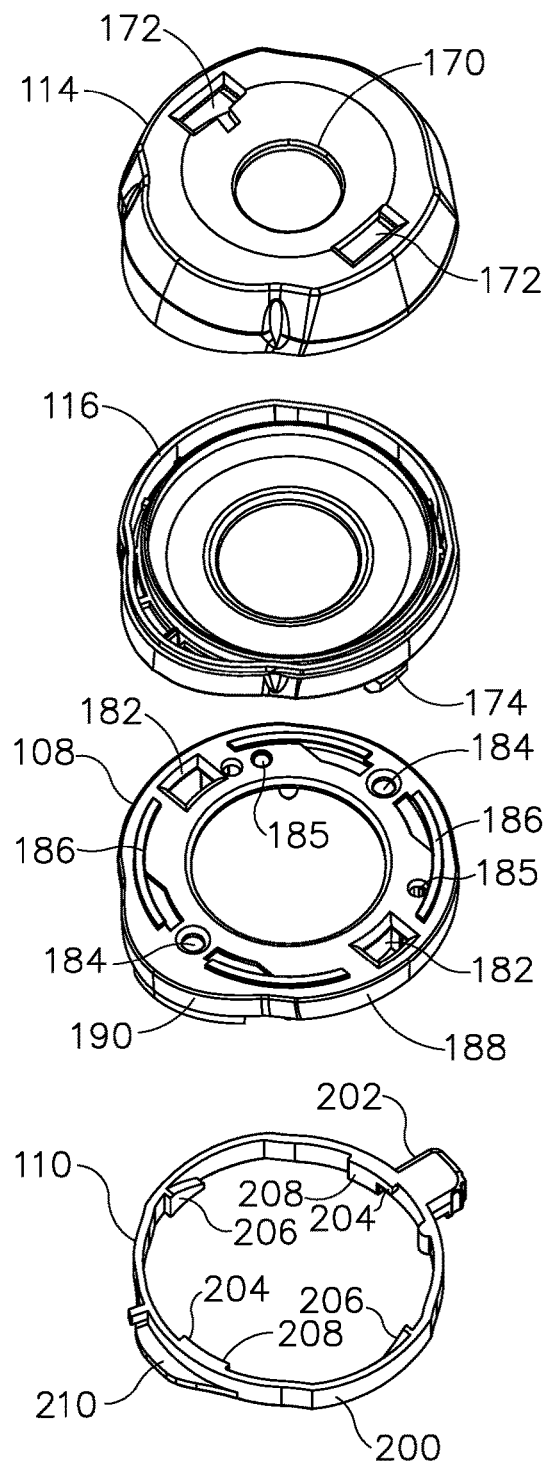
FIG. 7A depicts an exploded top perspective view of a portion of the trocar housing of FIG. 5A.
Figure 7B:
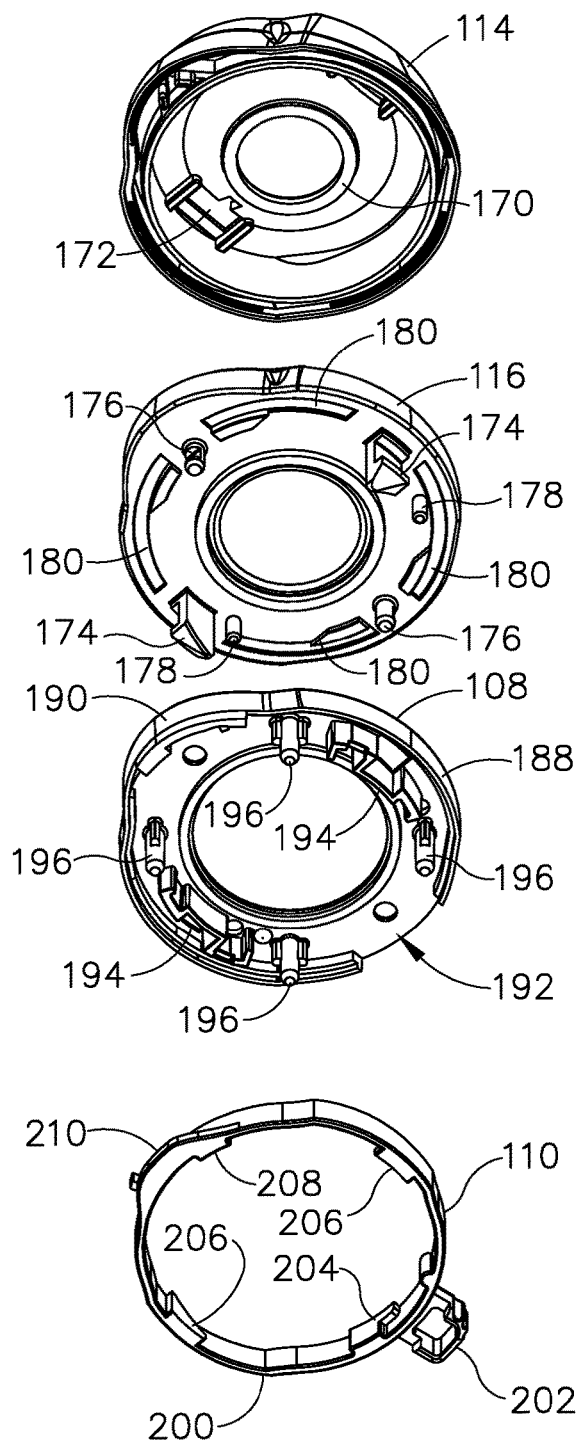
FIG. 7B depicts an exploded bottom perspective view of the housing portion of FIG. 7A.
Figure 8:
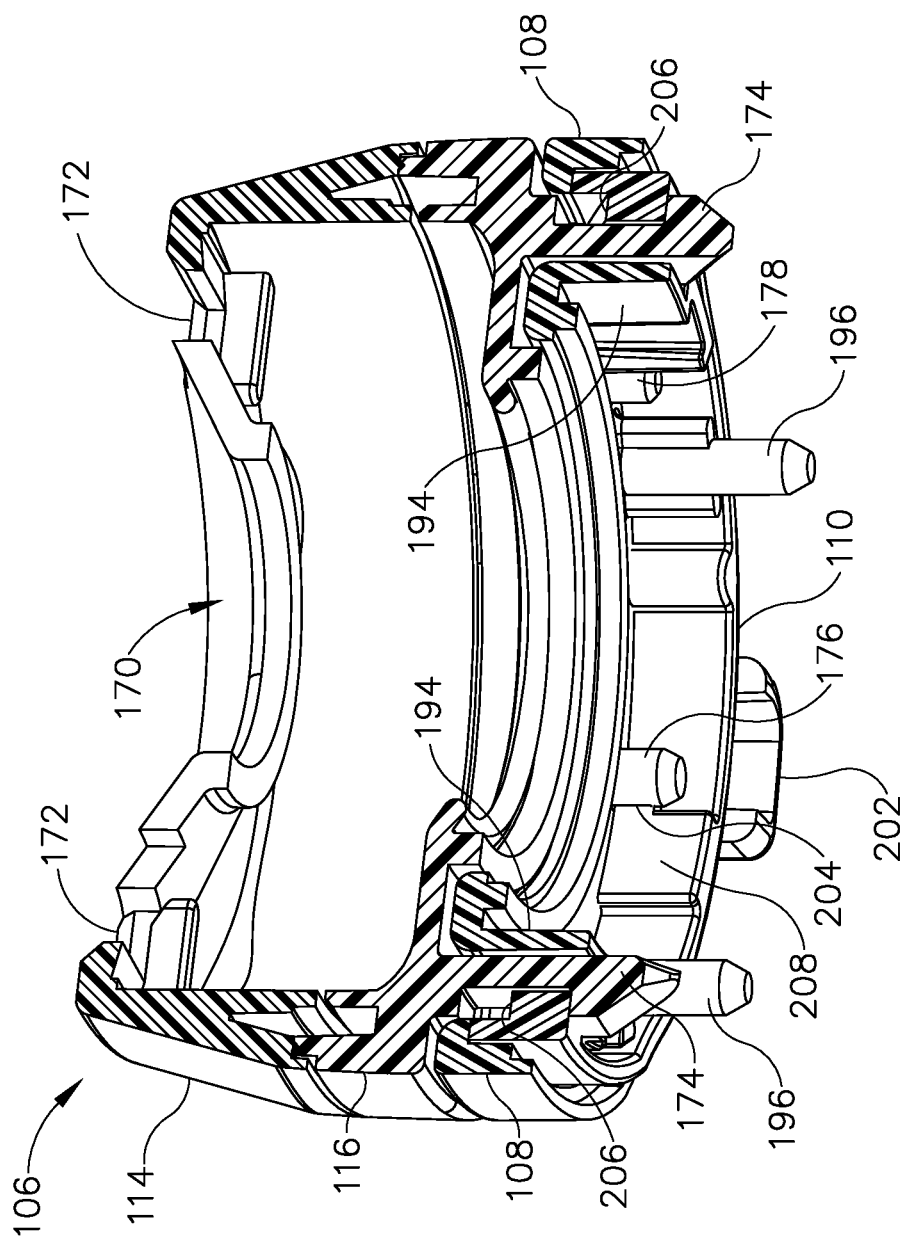
FIG. 8 depicts an assembled side sectional perspective view of the housing portion of FIG. 7A.

FIGS. 7A-8 show additional details of proximal housing head (114), proximal housing base (116), housing cap plate (108), and latch ring (110). Proximal housing head (114) includes a central opening (170) that defines a proximal end of working channel (132) of trocar (100). Proximal housing head (114) further includes a pair of slots (172) configured to receive a corresponding pair of tabs extending distally from the proximal head of an obturator, such as tabs (32) of obturator (14), for releasably connecting the obturator to trocar (100). Proximal housing head (114) is supported by and coupled to proximal housing base (116), for example by a snap-fit connection. Though not shown, a proximal seal assembly, such as an instrument seal, may be arranged between proximal housing head and proximal housing base (116). Such a proximal seal assembly may cooperate with distal seal assembly (140), described above, to ensure a sealing engagement between trocar (100) and a surgical instrument inserted through trocar (100) while maintaining insufflation.

As described below, proximal housing (106), defined by proximal housing head (114) and proximal housing base (116), is configured to couple with and selectively decouple from the remaining distal portion of trocar (100) via operation of latch ring (110) in combination with housing cap plate (108). In that regard, proximal housing base (116) further includes a plurality of distally extending mating features configured to facilitate attachment and release of proximal housing (106) from housing cap plate (108) and latch ring (110). In particular, an underside of proximal housing base (116) includes a pair of latching tabs (174), a pair of latching posts (176), a pair of guide pins (178), and a plurality circumferentially extending arcuate recesses (180). In the present example, four arcuate recesses (180) are provided in respective quadrants of the underside of proximal housing base (116). Additionally, latching tabs (174) are arranged at diametrically opposed positions along a first transverse axis, and latching tabs (174) are arranged at diametrically opposed positions along a second transverse axis that is perpendicular to the first transverse axis. Each guide pin (178) is positioned circumferentially between a latching tab (174) and an adjacent latching post (176). In other examples, various alternative quantities and arrangements of latching tabs (174), latching posts (176), guide pins (178), arcuate recesses (180), and/or other like mating features, and corresponding mating features of housing cap plate (108) and latch ring (110) described below, may be provided.

As shown in FIG. 7A, housing cap plate (108) includes a plurality of mating features configured and positioned to receive the above-described features of proximal housing base (116) to promote coupling and rotational alignment of proximal housing (106) with housing cap plate (108) and latch ring (110). In particular, housing cap plate (108) includes a pair of tab slots (182) configured to receive latching tabs (174) therethrough, a pair of post bores (184) configured to receive latching posts (176) therethrough, a pair of pin bores (185) configured to receive guide pins (178) therethrough, and a plurality of circumferentially extending arcuate ribs (186) configured to seat within arcuate recesses (180). As described above, various alternative quantities and arrangements of these mating features may be provided in other examples.

Housing cap plate (108) further includes a downwardly depending sidewall (188) extending about an outer perimeter of housing cap plate (108). A section of sidewall (188) bulges radially outwardly to define a nose portion (190) of housing cap plate (108) that is centered on the axis along which post bores (184) and latching posts (176) are arranged. As shown in FIG. 5A, nose portion (190) aligns with and overhangs a portion of insufflation port (134). As shown in FIG. 7B, housing cap plate (108) further includes a circumferentially extending slot (192) formed in sidewall (188) at a location opposite of nose portion (190). Slot (192) is configured to expose a user engagement feature projecting radially outwardly from latch ring (110), as described below.

As shown in FIGS. 7B and 8, an underside of housing cap plate (108) includes a pair of distally extending tab retaining walls (194) aligned with tab slots (182) and configured to abut and circumferentially constrain latching tabs (174) when tabs (174) are inserted through tab slots (182). The underside of housing cap plate (108) additionally includes a plurality of distally extending coupling posts (196) configured to be received by a corresponding plurality of coupling bores (198) formed on distal housing (112), as shown in FIG. 6, for coupling housing cap plate (108) with distal housing (112). In exemplary configurations, coupling posts (196) and coupling bores (198) may be suitably shaped and sized respectively to couple with a press-fit or a snap-fit engagement.

As shown in FIGS. 7A-8, latch ring (110) includes an annular body (200) and a user engagement feature in the form of a knob (202) projecting radially outwardly from annular body (200). Latch ring (110) further includes a plurality of latching features projecting radially inwardly from annular body (200). In particular, latch ring (110) includes a pair of latching arms (204) arranged at diametrically opposed positions along a first transverse axis, and a pair of cam ramps (206) arranged at diametrically opposed positions along a second transverse axis that is generally perpendicular to the first transverse axis. Each latching arm (204) extends circumferentially from an adjoining base (208) that may function as a secondary rotational stop for latch ring (110), as described below. Latch ring (110) additionally includes an arcuate fin (210) configured to be received and move circumferentially within nose portion (190) of housing cap plate (108). Knob (202) and arcuate fin (210) are generally diametrically opposed from one another across annular body (200).

Latch ring (110) is arranged distally of housing cap plate (108) and is housed radially inwardly of housing cap plate sidewall (188) at a proximal end, as best shown in FIG. 8, and radially inwardly of distal housing (112) at a distal end, as shown in FIG. 11. Latch ring (110) is rotatable about the central axis of trocar (100) between a latched position (see FIG. 9A) in which the latching features of latch ring (110) capture the distally extending features of proximal housing base (116), and an unlatched position (see FIG. 10A) in which the latching features of latch ring (110) release the distally extending features of proximal housing base (116) to thereby allow proximal detachment of proximal housing (106). Latch ring (110) is movable between the latched and unlatched positions by knob (202), which projects radially through circumferential slot (192) of housing cap plate (108) and is movable circumferentially therein as latch ring (110) rotates about the trocar central axis. In particular, circumferential slot (192) may define the rotational range of latch ring (110) such that a first end of slot (192) defines the latched position and a second end of slot (192) defines the unlatched position. In various configurations, proximal housing base (116), housing cap plate (108), and latch ring (110) may be suitably configured to define any desired rotational range of latch ring (110) relative to proximal housing base (116) and housing cap plate (108), which remain rotationally fixed.

FIG. 8 shows latch ring (110) in an exemplary latched position. As latch ring (110) is rotated into this latched position, from an unlatched position, each cam ramp (206) is received within an outwardly facing notch of a respective latching tab (174) of proximal housing base (116). Simultaneously, each latching arm (204) is received within an outwardly facing notch (see FIG. 7B) of a respective latching post (176) of proximal housing base (116). As latch ring (110) is rotated further toward the latched position, the sloped surface of each cam ramp (206) engages a proximal notch wall of the respective latching tab (174), and the latching arms (204) advance further within the notches of their respective latching posts (176), thereby securing proximal housing (106) axially against housing cap plate (108). Latch ring (110) may be rotated in the opposite direction to disengage cam ramps (206) from latching tabs (174) and latching arms (204) from latching posts (176), to thereby enable proximal detachment of proximal housing (106) from the remaining distal portion of trocar (100).

Rotation of latch ring (110) between the latched and unlatched positions is limited by direct contact of latch ring knob (202) with the ends of circumferential slot (192) formed in housing cap plate (108), which serves as a primary rotational stop. One or more secondary rotational stops may also be provided. For example, a side surface of each latching arm base (208) is configured to about a respective latching post (176) of proximal housing base (116), and a first end of fin (210) is configured to about a corresponding first inner surface of distal housing (112) (see FIG. 9A), to prevent rotation of latch ring (110) beyond the latched position. A second end of fin (210) may be configured to about a corresponding second inner surface of distal housing (112) (see FIG. 10A) to prevent rotation of latch ring (110) beyond the unlatched position. Though not shown, latch ring (110) may be coupled with a resilient member configured to bias latch ring (110) toward the latched position.

FIGS. 9A-10B show rotation of latch ring (110) relative to the remainder of trocar (100), including proximal housing base (116) and housing cap plate (108), between the latched position (FIGS. 9A-9B) and the unlatched position (FIGS. 10A-10B). FIG. 9A shows latch ring (110) in the latched position in which cam ramps (206) and latching arms (204) engage latching tabs (174) and latching posts (176), respectively, of proximal housing base (116). As shown in FIG. 9B, this position of latch ring (110) maintains proximal housing (106) in axial engagement with the remaining distal portion of trocar (100). FIG. 10A, by comparison, shows latch ring (110) after having been rotated to the unlatched position such that cam ramps (206) and latching arms (204) disengage latching tabs (174) and latching posts (176), respectively. As shown in FIG. 10B, this position of latch ring (110) enables proximal housing (106) to be removed proximally from the remaining distal portion of trocar (100).

As shown in FIGS. 9A and 10A, needle guide tubes (160) are oriented at diametrically opposed positions along a first axial plane (P1) extending along and through (i.e., containing) the central axis of trocar (100). Additionally, latch ring (110) is oriented such that knob (202) is movable within circumferential slot (192) along a circumferential path having a midpoint (M) that is diametrically opposed from insufflation port (134) along a second axial plane (P2) extending along and through the central axis of trocar (100). In the present example, first axial plane (P1) and second axial plane (P2) are perpendicular to one another. Accordingly, path midpoint (M) is spaced circumferentially equidistantly between needle guide tubes (160) and their respective needle ports (150, 152); specifically, at approximately 90 degrees in the present example. Consequently, latch ring knob (202) remains circumferentially spaced (or "offset") from needle guide tubes (160) and needle ports (150, 152) throughout the full range of permissible rotation of latch ring (110). Advantageously, this configuration prevents undesirable interference between knob (202) and a suture passer needle being directed through needle guide tubes (160) and needle ports (150, 152), as shown in FIG. 11.

As used herein with reference to various first and second structures or reference points, such as path midpoint (M) and insufflation port (134) described above, the term "diametrically opposed" encompasses but is not limiting to a configuration in which the referenced structures or reference points are located at the same longitudinal location along the central axis of trocar (100). Indeed, in the present example shown throughout FIGS. 5A-10B, path midpoint (M) for latch ring knob (202) is spaced proximally from insufflation port (134), though midpoint (M) and port (134) are still understood to be diametrically opposed from one another along axial plane (P2), shown in FIGS. 9A and 10A.

Those of ordinary skill in the art will recognize that various other configurations of housing (102) and cannula (104) as described above may be provided such that latch ring knob (202) remains circumferentially spaced (or "offset") from needle guide tubes (160) and needle entrance ports (150) throughout the full range of permissible rotation of latch ring (110). In such alternative configurations, midpoint (M) of the circumferential path along which knob (202) travels may or may not be spaced circumferentially equidistantly between needle guide tubes (160) and needle entrance ports (150). In various examples, path midpoint (M) may be circumferentially spaced from one or more of needle guide tubes (160) and the respective needle entrance port (150) by less than, greater than, or equal to 90 degrees. Furthermore, in other examples as described above, needle guide tubes (160) and their respective needle entrance ports (150), and/or needle exit ports (152), may be positioned in non-diametrically opposed arrangements.

FIG. 11 shows a side sectional view of trocar (100) with an exemplary suture passer needle (220) inserted therethrough along an oblique suture path extending through needle guide tube (160), needle entrance port (150), across working channel (132), and through needle exit port (152). As described above, each oblique suture path passing through trocar (100) includes a plurality of pierceable seals, including a guide tube entrance seal (164), a needle entrance port seal (154), and a needle exit port seal (156). Each seal (154, 156, 164) is configured to assist in maintaining insufflation when suture passer needle (220) is inserted through trocar (100) along the suture path, and/or when suture passer needle (220) is withdrawn from trocar (100).

Figure 12A:
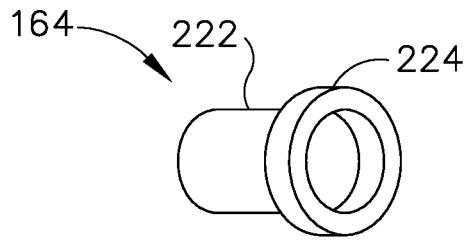
FIG. 12A depicts a perspective view of an exemplary pierceable seal provided at the entrance ends of first and second needle guide tubes of the trocar of FIG. 5A.

As described above, the guide tube entrance seals of the present example are shown in the form of seal caps (164). FIG. 12A shows additional details of seal cap (164), which includes a cylindrical body (222) and a proximal rim (224) defining a proximal opening to seal cap (164). Cylindrical body (222) is formed with an outer diameter sized to be received within a proximal end of a needle guide tube (160), and includes a closed distal end that is pierceable by suture passer needle (200), as shown in FIG. 11. Cylindrical body (222) and proximal rim (224) define an inner diameter sized to sealingly engage an outer surface of suture needle passer (220) upon insertion through trocar (100).

Figure 12B:
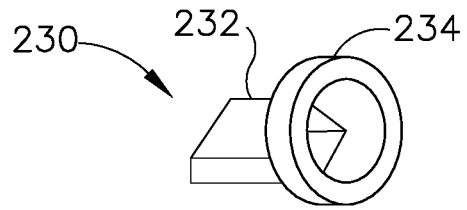
FIG. 12B depicts a perspective view of another exemplary pierceable seal provided at the entrance ends of first and second needle guide tubes of the trocar of FIG. 5A.

FIG. 12B shows another exemplary seal cap (230) having a body (232) and a proximal rim (234) defining a proximal opening to seal cap (230). Body (232) may be in the form of a duckbill seal or a tab having a closed distal end, for example. Proximal rim (234) defines a first inner dimension of seal cap, and body (232) defines a second smaller inner dimension of seal cap (230). In some variations, the second inner dimension defined by body (232) may taper distally. Seal caps (164, 230) described above may be formed separately from housing (102) and cannula (104) and assembled with needle guide tubes (160) during manufacture of trocar (100). In other examples, seal caps (164, 230) may be co-molded with needle guide tubes (160) in a single operation.

B. Exemplary Needle Guide Tubes

Figure 13:
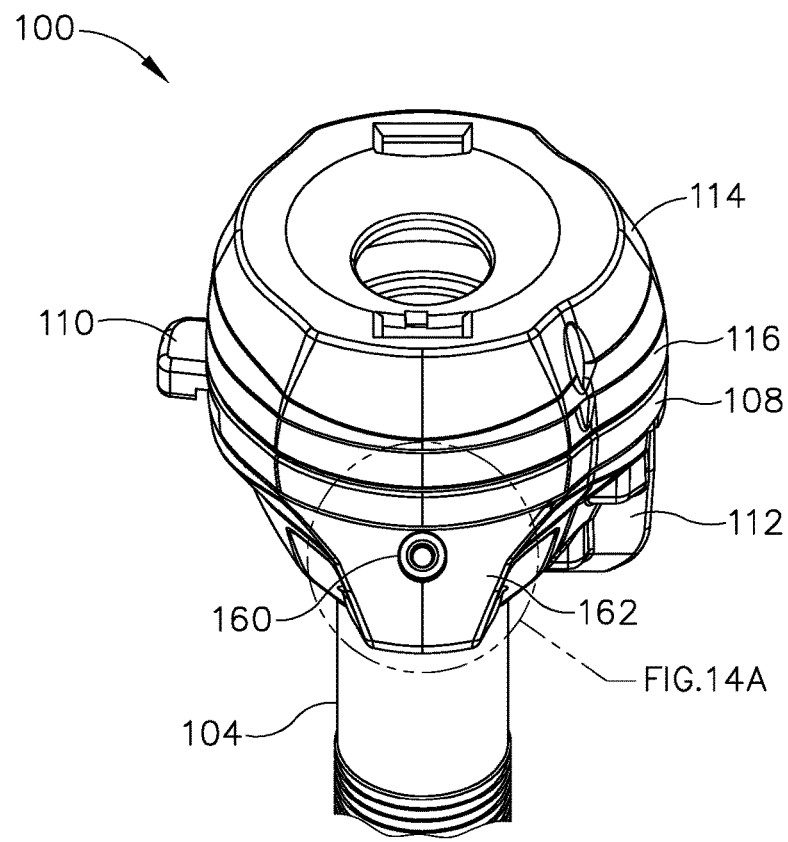
FIG. 13 depicts a side perspective view of the trocar of FIG. 5A.
Figure 14A:
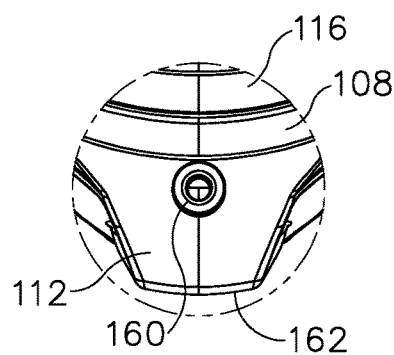
FIG. 14A depicts an enlarged perspective view of a region indicated in FIG. 13, showing details of a needle guide tube of the trocar.
Figure 14B:
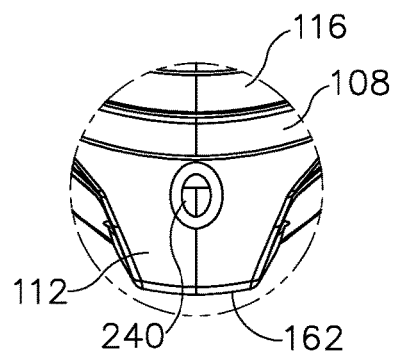
FIG. 14B depicts an enlarged perspective view showing details of a needle guide tube shaped according to an exemplary variation of the needle guide tube of FIG. 14A.
Figure 14C:
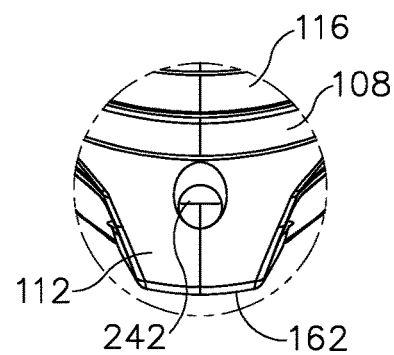
FIG. 14C depicts an enlarged perspective view showing details of a needle guide tube shaped according to another exemplary variation of the needle guide tube of FIG. 14A.

FIGS. 13 and 14A show additional details of needle guide tubes (160) of trocar (100). In the present example, needle guide tubes (160) are formed with a generally circular cross-section. In other examples, needle guide tubes (160) may be formed with various alternatively shaped cross-sections to facilitate insertion of suture passer needles. For example, FIG. 14B shows an exemplary alternative configuration in which distal housing (112) is provided with needle guide tubes (240) having a generally oval cross-section. FIG. 14C shows another exemplary configuration in which distal housing (112) is provided with needle guide tubes (242) having entrance ends that are recessed inwardly within an outer surface of side wings (162), which may also serve to ease insertion of suture passer needles. Guide tubes (242) may be provided with any suitably shaped cross-section, such as a circular cross-section, for example.

C. Exemplary Suturing Procedure Using Trocar Having Needle Ports

FIGS. 15A-15E schematically illustrate steps of an exemplary procedure for suturing closed an opening (58) (see FIG. 15D) formed in tissue (17) by trocar (100) during insertion for accessing body cavity (18). Advantageously, the features of trocar (100) described above enable a surgeon to leave trocar (100) in place within opening (58) and use trocar (100) as a needle guide mechanism for directing suture thread (250) distally through tissue (17) and into cavity (18) at desired suture angles to achieve an appropriate degree of "tissue bite" in lower fascia layers (56) of tissue (17). As used herein, the term "tissue bite" refers to the amount of tissue (17) captured by a suture thread. In the present context, tissue bite is defined by a distance (X) (see FIG. 15E) measured perpendicularly from the inner wall of tissue opening (58), which may coincide with the outer surface of cannula (104), to the point at which a suture passer needle and thus suture thread (250) exits distally from fascia (56) into body cavity (18).

FIG. 15A shows trocar cannula (104) extending distally through a portion of upper fat layers (54) and through a full thickness of lower fascia layers (56) of patient tissue (17), and into body cavity (18). All surgical instruments (not shown) have been withdrawn from trocar (100) such that working channel (132) is clear. FIG. 15B shows insertion of an exemplary suture passer needle (252) distally through a needle guide tube (160) and along the respective first suture path as generally described above. A distal tip (254) of suture passer needle (252) carries an end (256) of suture thread (250) along the suture path, through fascia (56) and into body cavity (18). As described above, needle guide tubes (160) and needle ports (150, 152) are positioned such that the resulting suture paths are angled obliquely relative to the central axis of trocar (100).

Once suture thread end (256) has been delivered into cavity (18), suture passer needle (252) releases suture thread end (256) and is withdrawn proximally from trocar (100). As shown in FIG. 15C, suture passer needle (252) is then re-inserted distally through the opposing needle guide tube (160) and along the respective second suture path into cavity (18). Suture passer needle (252) is then manipulated by a surgeon to recapture suture thread end (256) with needle tip (254). Once captured, thread end (256) and needle are withdrawn proximally through trocar (100) along the second suture path.

FIG. 15D shows trocar (100) and suture thread (250) following proximal removal of suture passer needle (252) along the second suture path. In the present configuration, suture thread (250) includes a first thread leg (258) passing distally along the first suture path and through a first captured portion of fascia (56) located on a first side of tissue opening (58); a second thread leg (260) passing distally along the second suture path and through a second captured portion of fascia (56) located on a second side of tissue opening; and an anchoring loop (262) extending through cavity (18) between the first and second captured portions of fascia (56). As shown in FIG. 15D, trocar (100) is withdrawn proximally from tissue opening (58) to allow thread legs (258, 260) to advance distally through needle guide tubes (160) and along their respective suture paths, thereby releasing suture thread (250) from trocar (100).

As shown in FIG. 15E, once trocar (100) has been fully disengaged from suture thread (250), thread legs (258, 260) may be pulled tight to draw together fascia (56) on either side of tissue opening (58), and then tied to form a suture knot (264) at a location just proximally of fascia layers (56). Optionally, the remaining portions of thread legs (258, 260) may be directed through fat layers (54) and skin (52) using suture needles, for example as shown in FIG. 4D using needles (62), to create an additional "superficial" suture knot to fully close tissue opening (58) and promote healing.

Figure 16A:
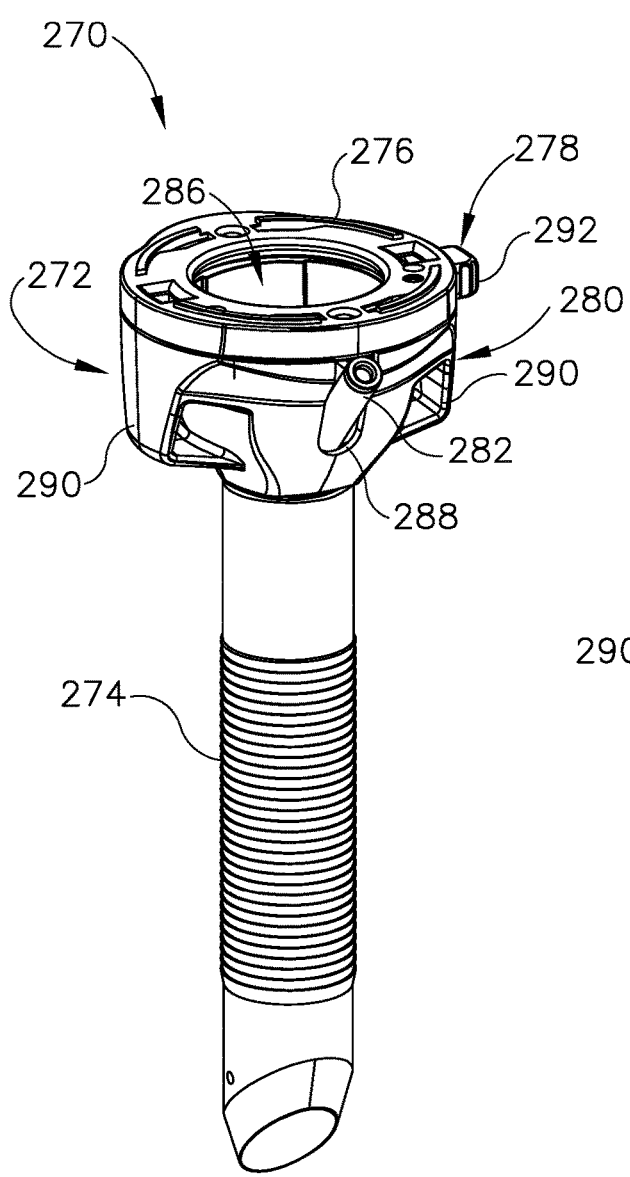
FIG. 16A depicts a perspective view of another exemplary trocar having needle guide tubes that are integrally molded with the cannula.
Figure 16B:
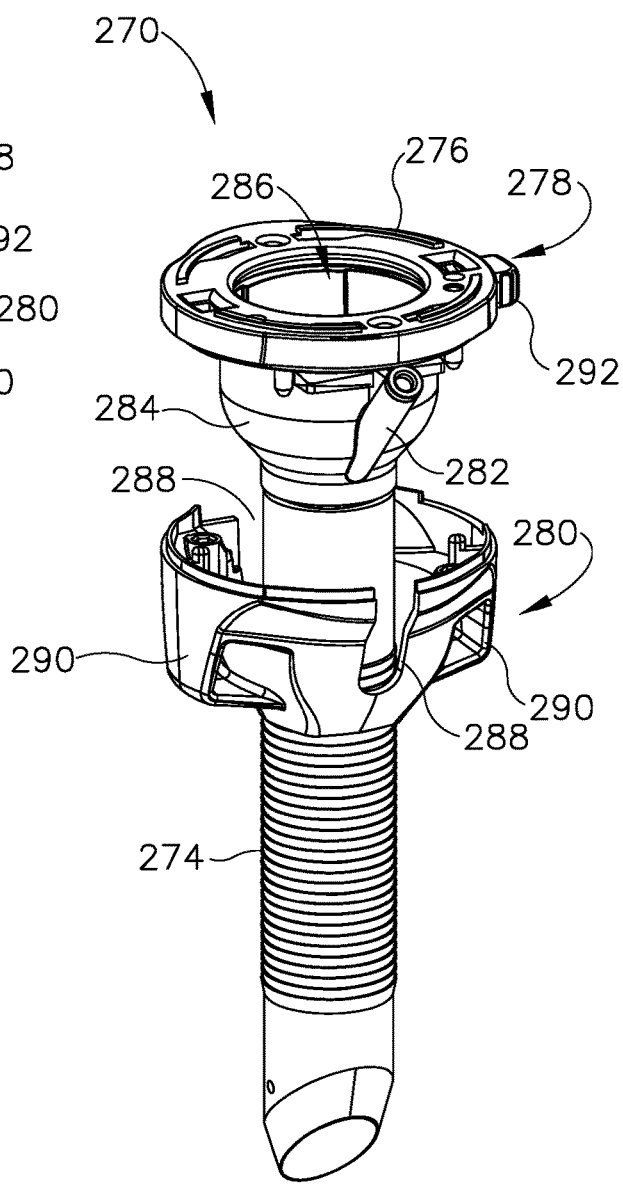
FIG. 16B depicts a partially disassembled perspective view of the trocar of FIG. 16A.

III. Exemplary Trocar Having Distal Housing with Integrally Formed Needle Guide Tubes FIGS. 16A and 16B show another exemplary trocar (270). Trocar (270) is similar to trocar (100) in that trocar (270) includes a housing (272) and a cannula (274) coupled to and extending distally from housing (272) along a central axis of trocar (270). Housing (272) includes a proximal housing (not shown), a housing cap plate (276), a latch ring (278), and a distal housing (280). These components are substantially similar in structure and function to the corresponding components of trocar (100) described above, except as otherwise described below. In particular, trocar (270) includes first and second needle guide tubes (282) that are formed integrally with proximal hub (284) of cannula (274), rather than with distal housing (280). Distal ends of needle guide tubes (282) open directly to a working channel (286) of trocar (270), and thus needle guide tubes (282) define the needle entrance ports to working channel (286). Plug seals (154) received within needle entrance ports (150) of trocar (100) may be omitted from trocar (270).

Distal housing (280) of trocar (270) includes a pair of axially extending slots (288) sized and shaped to accommodate needle guide tubes (282) therethrough when distal housing (280) is connected to housing cap plate (276) during device assembly. In the present example, distal housing (280) is oriented such that slots (288) are arranged in sidewalls of distal housing (280) extending between side wings (290) of distal housing (280). In alternative configurations, slots (288) may be arranged in side wings (290) or in various other portions of distal housing (280). Similar to trocar (100) described above, trocar (270) is configured such that a knob (292) of latch ring (278) remains circumferentially spaced from each of needle guide tubes (282) throughout a full range of permissible rotation of latch ring (278) relative to housing cap plate (276). As described above in connection with trocar (100), such a configuration ensures unobstructed access to needle guide tubes (282) during use.

Figure 17:
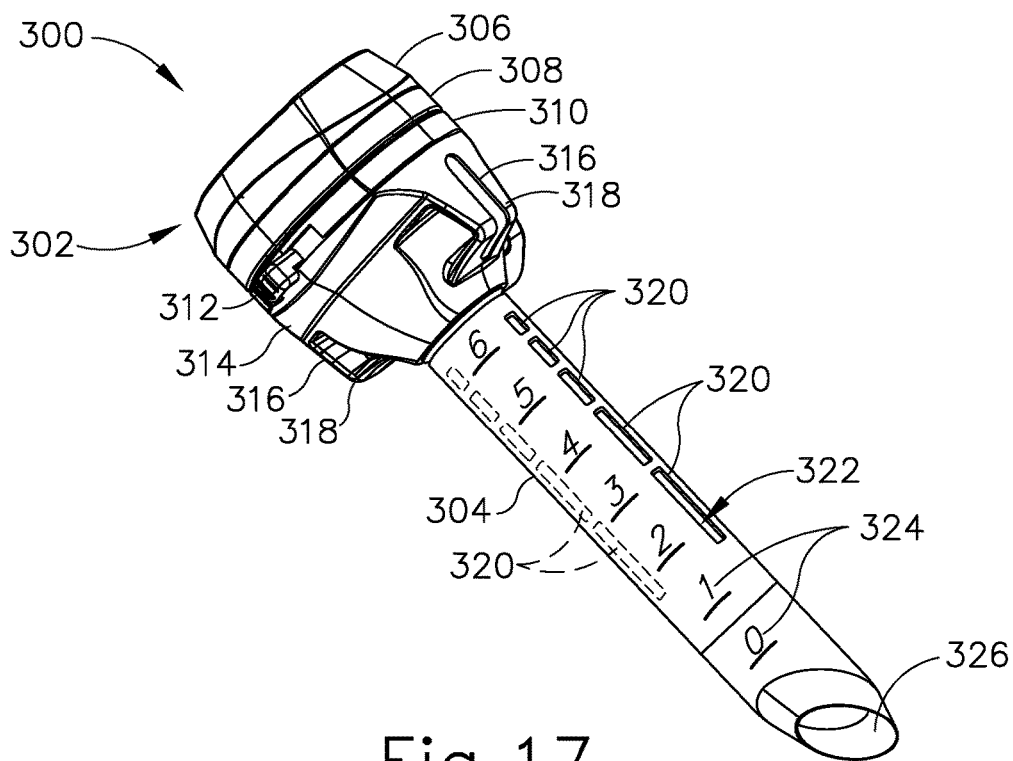
FIG. 17 depicts a perspective view of another exemplary trocar including a housing and a cannula having a plurality of axially spaced needle ports and corresponding indicia.

IV. Exemplary Trocar Having Suturing Features for Use with Various Tissue Thicknesses FIG. 17 shows another exemplary trocar (300) configured for use with patient tissue of various thicknesses. Trocar (300) is similar to trocar (100) in that trocar (300) includes a housing (302) and a cannula (304) coupled to and extending distally from housing (302) along a central axis of trocar (300). Housing (302) includes a proximal housing having a proximal housing head (306) and a proximal housing base (308), a housing cap plate (310), a latch ring (312), and a distal housing (314). These components are substantially similar in structure and function to the corresponding components of trocar (100) described above, except as otherwise described below. In particular, distal housing (314) includes needle guide structures in the form of slots (316) formed in side wings (318). Additionally, cannula (304) includes a plurality of elongate needle ports (320) spaced axially along opposing sides of cannula (304). Each needle port (320) is provided with a pierceable seal (322), which may include an axial slit (not shown) to ease passage of a suture passer needle through seal (322).

Cannula (304) of trocar (300) further includes visual indicia shown in the form of tissue depth graduation marks (324) spaced axially along a length of cannula (304). Marks (324) may indicate any suitable distance increments, such as inches or centimeters for example, and subdivisions of each increment. Marks (324) are configured to communicate to a surgeon a depth, measured from cannula tip (326), to which cannula (304) has been inserted within patient tissue. For example, during or after insertion of cannula (304) into tissue, a surgeon may observe a distal-most mark (324) that is visible extracorporeally to determine a depth to which cannula (304) has been inserted into the tissue, which may indicate a thickness of the tissue. Those of ordinary skill in the art will appreciate that any one or more of the features of trocar (300) may be incorporated into any of the other exemplary trocars described herein.

Figure 18A:
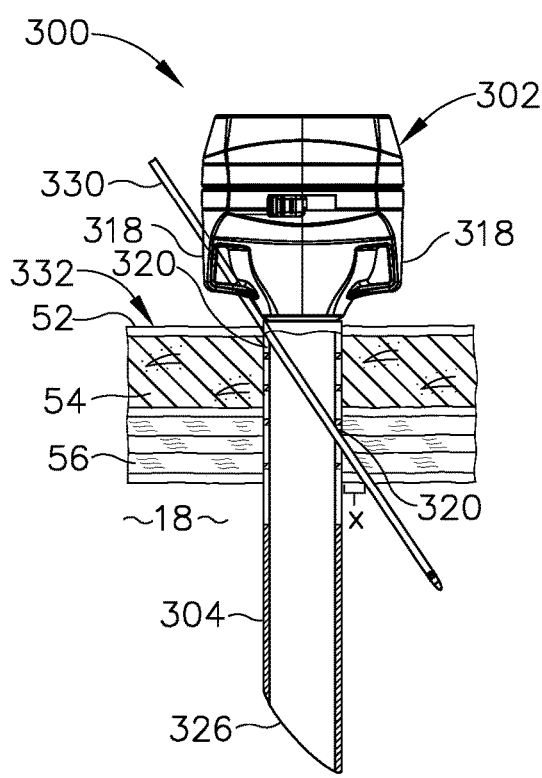
FIG. 18A depicts a schematic side sectional view of the trocar of FIG. 17 positioned within tissue of a first thickness, showing a suture passer device extending distally through the trocar and tissue along a first exemplary suture path defining a first oblique angle relative to a central axis of the trocar.
Figure 18B:
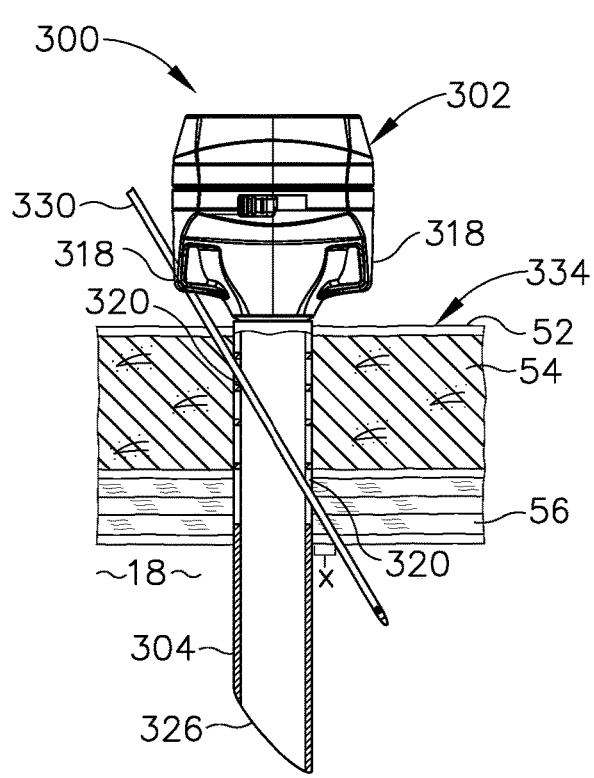
FIG. 18B depicts a schematic side sectional view of the trocar of FIG. 17 positioned within tissue of a second thickness, showing the suture passer device extending distally through the trocar and tissue along a second exemplary suture path defining a second oblique angle relative to the central axis of the trocar.

As shown in FIGS. 17-18B, elongate needle ports (320) increase in length along cannula (304) to allow a suture passer needle (330) to be directed through trocar (300) at a selected suture path angle, measured relative to a central axis of trocar (300), of a plurality of available suture path angles. This enables trocar (300) to be used as a suturing guide mechanism with tissues exhibiting a range of tissue thicknesses, while maintaining a consistent tissue bite distance (X) across the range of tissue thickness. FIG. 18A shows trocar (300) inserted through tissue (332) of a first thickness. Suture needle passer (330) is inserted through a first pair of needle ports (320) to define a first suture path angle and a tissue bite distance (X). FIG. 18B shows trocar (300) inserted through tissue (334) of a greater thickness than tissue (332). Suture needle passer (330) is inserted through a second pair of needle ports (320) to define a second suture path angle while maintaining substantially the same tissue bite distance (X) shown in FIG. 18A.

V. Exemplary Trocar for Applying Multiple Sutures at Same Surgical Site

In some instances, it may be desirable to apply multiple suture threads for closing an opening formed in patient tissue by a trocar cannula. For example, in instances in which the tissue opening is formed by a trocar cannula having a diameter of approximately 15 mm or greater, application of multiple suture threads may ensure effective closing of the tissue opening to promote complete and proper healing of the tissue. Accordingly, it may be desirable to provide one or more variations of any of the above-described trocars that includes suture features of suitable quantity and arrangement to facilitate application of multiple suture threads for closing a tissue opening.

FIGS. 19-21 show an exemplary variation of trocar (100) in the form of trocar (340), having suture features configured to facilitate application of first and second suture threads for closing a single tissue opening formed by trocar (340). Trocar (340) is similar to trocar (100) in that trocar (340) includes a housing (342) and a cannula (344) coupled to and extending distally from housing (342) along a central axis of trocar (340). Housing (342) includes a proximal housing (346), a housing cap plate (348), a latch ring (350) having a user engagement feature (352), and a distal housing (354). Cannula (344) and housing together define a working channel (356) extending through trocar (340) along the central axis thereof. These components of trocar (340) are substantially similar in structure and function to the corresponding components of trocar (100) described above, except as otherwise described below. For example, like trocar (100), trocar (340) includes a distal seal assembly (358), shown in FIG. 19, that separates a lumen of cannula (344) from an interior of housing (342). However, unlike distal seal assembly (140) of trocar (100), distal seal assembly (358) is shown in the form of a duckbill seal. Further, trocar (340) includes a proximal seal assembly (360) in the form of an instrument seal supported within proximal housing (346), as shown in FIG. 20.

Distal housing (354) of trocar (340) includes four needle guide tubes (362) defining respective needle entrance ports, and four needle exit ports (364) arranged on cannula (344), each needle exit port (364) corresponding to a respective needle guide tube (362). Each needle guide tube (362) and its respective needle exit port (364) defines a suture path, indicated by axes (A1, A2, A3, A4) in FIG. 21, extending distally through and obliquely relative to the central axis of trocar (340). Each needle port (362, 364) opens to working channel (356) and is sealed by a respective pierceable seal. Specifically, an entrance end of each needle guide tube (362) is sealed by a respective pierceable seal cap (366), which may be similar to seal caps (164, 230) described above. Each needle exit port (364) is sealed by a respective pierceable seal protrusion (368) projecting radially inwardly from an inner surface of a cannula sleeve (370), which may be similar to cannula sleeve (158) described above.

In the present example, latch ring (350) is oriented rotationally about the central axis of trocar (340) such that its user engagement feature (352) is generally diametrically opposed from an insufflation port (372). Additionally, needle guide tubes (362) and their respective needle exit ports (364) are arranged circumferentially about the central axis such that each needle guide tube (362) is circumferentially spaced from user engagement feature (352) and from insufflation port (372). As shown best in FIG. 20, user engagement feature (352) is spaced circumferentially equidistantly between a first pair of needle guide tubes (362), and insufflation port (372) is spaced circumferentially equidistantly between a second pair of needle guide tubes (362). Each needle exit port (364) is positioned to align with a respective needle guide tube (362) arranged along the corresponding suture path. In alternative examples, various other quantities and arrangements of needle guide tubes (362) and their respective needle exit ports (364) may be provided.

In use, each needle guide tube (362) and its respective needle exit port (364) cooperate with an opposed needle guide tube (362) and its needle exit port (364) to guide application of a suture thread (not shown) to tissue. Application of each of the first and second suture threads may be performed using the exemplary procedure described above in connection with FIGS. 15A-15D, for example. As is evident in FIG. 20, needle guide tubes (362) and needle exit ports (364) are circumferentially arranged such that the applied first and second suture threads cross over one another to define an X-shaped pattern in the tissue when viewed from above. It will be appreciated that any suitable circumferential spacing between needle guide tubes (362), and between needle exit ports (364), may be provided to achieve a desired suture pattern and resulting closure effect on the tissue opening.

Though not shown, the needle guide structures of any of the examples disclosed herein may be coupled to one or more rotatable structures configured to rotate about the central axis of the respective trocar. Examples of such a configuration are disclosed in U.S. patent application Ser. No. 15/637,688, entitled "Trocar with Oblique Needle Insertion Port and Coplanar Stopcock," filed on Jun. 29, 2017, published as U.S. Pat. Pub. No. 2019/0000503 on Jan. 3, 2019, issued as U.S Pat. No. 10,485,580 on Nov. 26, 2019, the disclosure of which is incorporated by reference herein. This rotating configuration enables the suture path corresponding to each needle guide structure to be selectively rotationally positioned about the trocar central axis during use. Further, such a configuration may include one or more detents or other rotational limiting mechanisms suitably positioned to define various pre-determined rotational positions of the one or more rotatable structures. The trocar cannula may be provided with a plurality of needle ports arranged circumferentially about the central axis to account for the various rotational positions of the needle guide structures. In various examples, the one or more rotatable structures may be incorporated within or coupled to the cannula or any portion of the housing, for instance.

The teachings presented herein may be further combined with various teachings of any one or more of the following: U.S. patent application Ser. No. 15/637,690, entitled "Needle Guide Instrument with Traverse Suture Capture Feature," filed on Jun. 29, 2017, published as U.S. Pat. Pub. No. 2019/0000443 on Jan. 3, 2019, the disclosure of which is incorporated by reference herein; U.S. patent application Ser. No. 15/637,702, entitled "Suture Grasping Instrument," filed on Jun. 29, 2017, published as U.S. Pat. Pub. No. 2019/0000440 on Jan. 3, 2019, the disclosure of which is incorporated by reference herein; U.S. patent application Ser. No. 15/637,712, entitled "Suture Passing Instrument with Puncture Site Identification Feature," filed on Jun. 29, 2017, published as U.S. Pat. Pub. No. 2019/0000444 on Jan. 3, 2019, the disclosure of which is incorporated by reference herein; U.S. patent application Ser. No. 15/637,696, entitled "Trocar Obturator with Transverse Needle Ports," filed on Jun. 29, 2017, published as U.S. Pat. Pub. No. 2019/0000506 on Jan. 3, 2019, the disclosure of which is incorporated by reference herein; U.S. patent application Ser. No. 15/637,707, entitled "Surgical Port with Wound Closure Channels," filed on Jun. 29, 2017, published as U.S. Pat. Pub. No. 2019/0000441 on Jan. 3, 2019, issued as U.S Pat. No. 10,568,619 on Feb. 25, 2020, the disclosure of which is incorporated by reference herein; U.S. patent application Ser. No. 15/637,735, entitled "Trocar Obturator with Detachable Rotary Tissue Fastener," filed on Jun. 29, 2017, published as U.S. Pat. Pub. No. 2019/0000502 on Jan. 3, 2019, the disclosure of which is incorporated by reference herein; U.S. patent application Ser. No. 15/637,778, entitled "Method of Suturing a Trocar Patch Incision," filed on Jun. 29, 2017, published as U.S. Pat. Pub. No. 2019/0000496 on Jan. 3, 2019, the disclosure of which is incorporated by reference herein; and/or other patents and patent application publications incorporated by reference herein.

VI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A surgical access device, comprising: (a) a cannula having a proximal end, a distal end, and a cannula lumen extending therebetween; (b) a housing assembly coupled to the proximal end of the cannula, wherein the housing assembly comprises: (i) a proximal housing, and (ii) a latch ring arranged distally of the proximal housing and having a user engagement feature, wherein the latch ring is rotatable by the user engagement feature to selectively couple and decouple the proximal housing with the cannula, wherein an interior of the housing assembly communicates with the cannula lumen to define a working channel extending from a proximal end of the surgical access device to a distal end of the surgical access device along a central axis thereof, wherein the working channel is configured to receive a surgical instrument therethrough; (c) a first needle port that opens to the working channel through a first side portion of the surgical access device; and (d) a second needle port that opens to the working channel through a second side portion of the surgical access device; wherein each of the first and second needle ports is configured to direct a suture passer needle through the surgical access device, across the working channel, at an oblique angle relative to the central axis of the surgical access device, wherein the user engagement feature of the latch ring is circumferentially offset from each of the first and second needle ports.

EXAMPLE 2

The surgical access device of Example 1, wherein the housing assembly further comprises a distal housing coupled to the cannula, wherein the latch ring is arranged between the proximal housing and the distal housing, wherein the latch ring is rotatable relative to at least one of the proximal or distal housings to selectively couple and decouple the proximal housing with the distal housing.

EXAMPLE 3

The surgical access device of any one or more of the preceding Examples, wherein the latch ring is rotatable to a position in which the user engagement feature is spaced circumferentially equidistantly between the first and second needle ports.

EXAMPLE 4

The surgical access device of any one or more of the preceding Examples, wherein the latch ring is rotatable to a position in which the user engagement feature is circumferentially offset from each of the first and second needle ports by at least 90 degrees.

EXAMPLE 5

The surgical access device of Example 4, wherein the first and second needle ports are diametrically opposed from one another, wherein the latch ring is rotatable to a position in which the user engagement feature is circumferentially offset from each of the first and second needle ports by 90 degrees.

EXAMPLE 6

The surgical access device of any one or more of the preceding Examples, further comprising an insufflation port configured to direct insufflation fluid into the working channel, wherein the latch ring is rotatable to a position in which the user engagement feature is diametrically opposed from the insufflation port.

EXAMPLE 7

The surgical access device of Example 6, wherein when the user engagement feature is positioned in diametric opposition to the insufflation port, the user engagement feature is spaced circumferentially equidistantly between the first and second needle ports.

EXAMPLE 8

The surgical access device of Example 7, wherein when the user engagement feature is positioned in diametric opposition to the insufflation port, the user engagement feature is circumferentially offset from each of the first and second needle ports by 90 degrees.

EXAMPLE 9

The surgical access device of any one or more of the preceding Examples, wherein the user engagement feature comprises an outwardly projecting knob.

EXAMPLE 10

The surgical access device of any one or more of the preceding Examples, wherein the cannula includes a proximal hub having a larger diameter than medial and distal portions of the cannula, wherein the first and second needle ports extend through the proximal hub.

EXAMPLE 11

The surgical access device of any one or more of the preceding Examples, wherein the first needle port comprises a first needle entrance port and the second needle port comprises a second needle entrance port, wherein the surgical access device further comprises a first needle exit port arranged distally of the first needle entrance port, and a second needle exit port arranged distally of the second needle entrance port, wherein the first needle entrance port and the first needle exit port together define a first suture path extending obliquely across the central axis of the surgical access device, wherein the second needle entrance port and the second needle exit port together define a second suture path extending obliquely across the central axis of the surgical access device.

EXAMPLE 12

The surgical access device of Example 11, wherein the first and second needle entrance ports and the first and second needle exit ports are arranged such that the first and second suture paths extend through the central axis of the surgical access device.

EXAMPLE 13

The surgical access device of any one or more of Examples 11 through 12, further comprising a first needle guide structure configured to guide a suture passer needle along the first suture path, and a second needle guide structure configured to guide a suture passer needle along the second suture path.

EXAMPLE 14

The surgical access device of any one or more of Examples 11 through 13, wherein each of the first and second needle entrance ports and each of the first and second needle exit ports is provided with a pierceable seal.

EXAMPLE 15

The surgical access device of Example 14, further comprising a sleeve that encircles at least a portion of the cannula, wherein the sleeve defines the pierceable seals for the first and second needle exit ports.

EXAMPLE 16

A surgical access device, comprising: (a) a cannula having a proximal end, a distal end, and a cannula lumen extending therebetween; (b) a housing assembly coupled to the proximal end of the cannula, wherein the housing assembly comprises: (i) a proximal housing, and (ii) a latch ring arranged distally of the proximal housing and having a user engagement feature, wherein the latch ring is movable by the user engagement feature to selectively couple and decouple the proximal housing with the cannula, wherein an interior of the housing assembly communicates with the cannula lumen to define a working channel extending from a proximal end of the surgical access device to a distal end of the surgical access device along a central axis thereof, wherein the working channel is configured to receive a surgical instrument therethrough; (c) a first needle port that opens to the working channel through a first side portion of the surgical access device; and (d) a second needle port that opens to the working channel through a second side portion of the surgical access device; wherein each of the first and second needle ports is configured to direct a suture passer needle through the surgical access device, across the working channel, at an oblique angle relative to the central axis of the surgical access device, wherein the user engagement feature of the latch ring is circumferentially offset from each of the first and second needle ports by at least 90 degrees.

EXAMPLE 17

The surgical access device of Example 16, wherein the user engagement feature is movable to a position in which the user engagement feature is spaced circumferentially equidistantly between the first and second needle ports.

EXAMPLE 18

The surgical access device of any one or more of Examples 16 through 17, wherein the user engagement feature comprises an outwardly projecting knob.

EXAMPLE 19

A surgical access device, comprising: (a) a cannula having a proximal end, a distal end, and a cannula lumen extending therebetween; (b) a housing assembly coupled to the proximal end of the cannula, wherein the housing assembly comprises: (i) a proximal housing, and (ii) a latch ring arranged distally of the proximal housing and having an outwardly projecting knob, wherein the latch ring is movable by the outwardly projecting knob to selectively couple and decouple the proximal housing with the cannula, wherein an interior of the housing assembly communicates with the cannula lumen to define a working channel extending from a proximal end of the surgical access device to a distal end of the surgical access device along a central axis thereof, wherein the working channel is configured to receive a surgical instrument therethrough; (c) an insufflation port configured to direct insufflation fluid into the working channel; (d) a first needle port that opens to the working channel through a first side portion of the surgical access device; and (e) a second needle port that opens to the working channel through a second side portion of the surgical access device; wherein each of the first and second needle ports is configured to direct a suture passer needle through the surgical access device, across the working channel, at an oblique angle relative to the central axis of the surgical access device, wherein the outwardly projecting knob of the latch ring is circumferentially offset from each of the first needle port, the second needle port, and the insufflation port.

EXAMPLE 20

The surgical access device of Example 19, wherein the user engagement feature is movable to a position in which the user engagement feature is diametrically opposed from the insufflation port and is circumferentially offset from at least one of the first or second needle ports by at least 90 degrees.

VII. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical access device, comprising:
   (a) a cannula having a proximal end, a distal end, and a cannula lumen extending therebetween through a medial portion of the cannula, wherein the proximal end includes a hub having a larger diameter than the distal end and the medial portion;
   (b) a housing assembly coupled to the proximal end of the cannula, wherein the housing assembly comprises:
      (i) a proximal housing, and
      (ii) a latch ring arranged distally of the proximal housing and having a user engagement feature, wherein the latch ring is rotatable by the user engagement feature to selectively couple and decouple the proximal housing with the latch ring and the cannula,
      wherein an interior of the housing assembly communicates with the cannula lumen to define a working channel extending from a proximal end of the surgical access device to a distal end of the surgical access device along a central axis thereof, wherein the working channel is configured to receive a surgical instrument therethrough;
   (c) a first needle port that opens to the working channel through a first side of the hub of the cannula; and
   (d) a second needle port that opens to the working channel through a second side of the hub of the cannula;
   wherein each of the first and second needle ports is configured to direct a suture passer needle through the surgical access device, across the working channel, at an oblique angle relative to the central axis of the surgical access device,
   wherein the user engagement feature of the latch ring is circumferentially offset from each of the first and second needle ports.

2. The surgical access device of claim 1, wherein the housing assembly further comprises a distal housing coupled to the cannula, wherein the latch ring is arranged between the proximal housing and the distal housing, wherein the latch ring is rotatable relative to at least one of the proximal or distal housings to selectively couple and decouple the proximal housing with the distal housing.

3. The surgical access device of claim 1, wherein the latch ring is rotatable to a position in which the user engagement feature is spaced circumferentially equidistantly between the first and second needle ports.

4. The surgical access device of claim 1, wherein the latch ring is rotatable to a position in which the user engagement feature is circumferentially offset from each of the first and second needle ports by 90 degrees.

5. The surgical access device of claim 4, wherein the first and second needle ports are diametrically opposed from one another.

6. The surgical access device of claim 1, further comprising an insufflation port configured to direct insufflation fluid into the working channel, wherein the latch ring is rotatable to a position in which the user engagement feature is diametrically opposed from the insufflation port.

7. The surgical access device of claim 6, wherein when the user engagement feature is positioned in diametric opposition to the insufflation port, the user engagement feature is spaced circumferentially equidistantly between the first and second needle ports.

8. The surgical access device of claim 7, wherein when the user engagement feature is positioned in diametric opposition to the insufflation port, the user engagement feature is circumferentially offset from each of the first and second needle ports by 90 degrees.

9. The surgical access device of claim 1, wherein the user engagement feature comprises an outwardly projecting knob.

10. The surgical access device of claim 1, wherein the first needle port comprises a first needle entrance port and the second needle port comprises a second needle entrance port, wherein the surgical access device further comprises a first needle exit port arranged distally of the first needle entrance port, and a second needle exit port arranged distally of the second needle entrance port, wherein the first needle entrance port and the first needle exit port together define a first suture path extending obliquely across the central axis of the surgical access device, wherein the second needle entrance port and the second needle exit port together define a second suture path extending obliquely across the central axis of the surgical access device.

11. The surgical access device of claim 10, wherein the first and second needle entrance ports and the first and second needle exit ports are arranged such that the first and second suture paths extend through the central axis of the surgical access device.

12. The surgical access device of claim 10, further comprising a first needle guide structure configured to guide a suture passer needle along the first suture path, and a second needle guide structure configured to guide a suture passer needle along the second suture path.

13. The surgical access device of claim 10, wherein each of the first and second needle entrance ports and each of the first and second needle exit ports is provided with a pierceable seal.

14. The surgical access device of claim 13, further comprising a sleeve that encircles at least a portion of the cannula, wherein the sleeve defines the pierceable seals for the first and second needle exit ports.

15. A surgical access device, comprising:
  (a) a cannula having a proximal end, a distal end, and a cannula lumen extending therebetween;
  (b) a housing assembly coupled to the proximal end of the cannula, wherein the housing assembly comprises:
    (i) a proximal housing,
    (ii) a distal housing secured to the cannula, and
    (iii) a latch member arranged distally of the proximal housing and having a user engagement feature, wherein the latch member is movable by the user engagement feature to selectively couple and decouple the proximal housing with the distal housing and the cannula,
    wherein an interior of the housing assembly communicates with the cannula lumen to define a working channel extending from a proximal end of the surgical access device to a distal end of the surgical access device along a central axis thereof, wherein the working channel is configured to receive a surgical instrument therethrough;
  (c) an insufflation port configured to direct insufflation fluid into the working channel;
  (d) a first needle port that opens to the working channel through a first side portion of the surgical access device; and
  (e) a second needle port that opens to the working channel through a second side portion of the surgical access device;
  wherein each of the first and second needle ports is configured to direct a suture passer needle through the surgical access device, across the working channel, at an oblique angle relative to the central axis of the surgical access device,
  wherein the latch member is movable to a position in which the user engagement feature is diametrically opposed from the insufflation port.

16. The surgical access device of claim 15, wherein the user engagement feature is configured to be spaced circumferentially equidistantly between the first and second needle ports when the latch member is positioned in diametric opposition to the insufflation port.

17. The surgical access device of claim 15, wherein the user engagement feature comprises an outwardly projecting knob.

18. A surgical access device, comprising:
  (a) a cannula having a proximal end, a distal end, and a cannula lumen extending therebetween;
  (b) a housing assembly coupled to the proximal end of the cannula, wherein the housing assembly comprises:
    (i) a proximal housing,
    (ii) a distal housing secured to the cannula, and
    (iii) a latch member arranged between the proximal housing and the distal housing and having an outwardly projecting knob, wherein the latch member is movable by the outwardly projecting knob to selectively couple and decouple the proximal housing with the distal housing and the cannula,
    wherein an interior of the housing assembly communicates with the cannula lumen to define a working channel extending from a proximal end of the surgical access device to a distal end of the surgical access device along a central axis thereof, wherein the working channel is configured to receive a surgical instrument therethrough;
  (c) an insufflation port configured to direct insufflation fluid into the working channel;
  (d) a first needle port that opens to the working channel through a first side portion of the surgical access device; and
  (e) a second needle port that opens to the working channel through a second side portion of the surgical access device;

wherein each of the first and second needle ports is configured to direct a suture passer needle through the surgical access device, across the working channel, at an oblique angle relative to the central axis of the surgical access device, wherein the outwardly projecting knob of the latch member is movable along a path having a path midpoint that is diametrically opposed from the insufflation port.

19. The surgical access device of claim 18, wherein the path midpoint is circumferentially offset from at least one of the first or second needle ports by 90 degrees.

20. The surgical access device of claim 18, wherein the first and second needle ports define a first axial plane, wherein the path midpoint and the insufflation port define a second axial plane that intersects the first axial plane perpendicularly at the central axis.

* * * * *